US012136237B2

(12) United States Patent
Buckland

(10) Patent No.: US 12,136,237 B2
(45) Date of Patent: Nov. 5, 2024

(54) APPARATUS FOR CALIBRATING RETINAL IMAGING SYSTEMS

(71) Applicant: Translational Imaging Innovations, Inc., Hickory, NC (US)

(72) Inventor: Eric L. Buckland, Hickory, NC (US)

(73) Assignee: Translational Imaging Innovations, Inc., Hickory, NC (US)

( * ) Notice: Subject to any disclaimer, the term of this patent is extended or adjusted under 35 U.S.C. 154(b) by 471 days.

(21) Appl. No.: 17/568,306

(22) Filed: Jan. 4, 2022

(65) Prior Publication Data

US 2022/0215584 A1 Jul. 7, 2022

Related U.S. Application Data

(60) Provisional application No. 63/133,897, filed on Jan. 5, 2021.

(51) Int. Cl.
*A61B 3/00* (2006.01)
*A61B 3/12* (2006.01)
(Continued)

(52) U.S. Cl.
CPC .............. *G06T 7/80* (2017.01); *A61B 3/0025* (2013.01); *A61B 3/12* (2013.01); *G06T 3/40* (2013.01);
(Continued)

(58) Field of Classification Search
CPC ........... A61B 3/0025; A61B 3/12; G06T 3/40; G06T 7/0012; G06T 7/60; G06T 7/80;
(Continued)

(56) References Cited

U.S. PATENT DOCUMENTS 9,008,391 B1 4/2015 Solanki et al.
2007/0038040 A1 2/2007 Cense et al.

FOREIGN PATENT DOCUMENTS

CN 107736872 A 2/2018
DE 102018207827 B3 8/2019
(Continued)

OTHER PUBLICATIONS

International Search Report and Written Opinion, PCT/US2020/011117, Apr. 21, 2022, 6 pages.
Agrawal et al., "Characterizing the point spread function of retinal OCT devices with a model eye-based phantom," Biomedical Optics Express, vol. 3, No. 5, May 1, 2012, pp. 1116-1126.
(Continued)

*Primary Examiner* — Jack Dinh
(74) *Attorney, Agent, or Firm* — Stanek Lemon Crouse & Meeks, PA

(57) ABSTRACT

A model eye for calibrating a retinal imaging system is provided including a backplane having a negative radius of curvature R centered on the optical axis and a clear aperture diameter D2; a distance h along the optical axis from the nodal point to the backplane; an unobstructed field of view 2θ; a closed fluid fillable housing; a mechanical system for mounting, aligning, and preserving spacings of the elements of the model eye; and a pattern applied to the backplane, the pattern having a rotational symmetry and a radial repeating unit, extending substantially across the clear aperture, that spatially modulates intensity of light reflected from, or transmitted through, a surface of the backplane. D2/D1 is greater than 2, an absolute value of R/h is greater than 0.5, and 2θ is greater than zero (0) degrees.

13 Claims, 37 Drawing Sheets

(51) Int. Cl.
  *G06T 3/40*    (2024.01)
  *G06T 7/00*    (2017.01)
  *G06T 7/60*    (2017.01)
  *G06T 7/80*    (2017.01)
  *G09B 23/28*   (2006.01)

(52) U.S. Cl.
  CPC .............. *G06T 7/0012* (2013.01); *G06T 7/60* (2013.01); *G09B 23/286* (2013.01); *G06T 2207/30041* (2013.01); *G06T 2207/30204* (2013.01)

(58) Field of Classification Search
  CPC .......... G06T 2207/30041; G06T 2207/30204; G09B 23/286
  See application file for complete search history.

(56) References Cited

FOREIGN PATENT DOCUMENTS

| | | |
|---|---|---|
| EP | 3520679 A1 | 7/2019 |
| KR | 102188918 B1 | 7/2020 |
| KR | 1020200091668 | 7/2020 |
| WO | 2020/198562 A1 | 10/2020 |

OTHER PUBLICATIONS

Jacobs et al., "Artificial pupils and Maxwellian view," Applied Optics, vol. 31, No. 19, Jul. 1, 1992. pp. 3668-3677.
Kaschke et al. Optical Devices in Ophthalmology and Optometry, Chapter 2, Optics of the Human Eye, Nov. 11, 2013, pp. 15-48.
Leibowitz, Herschel, "The Use and Calibration of the 'Maxwellian View' in Visual Instrumentation," The American Journal of Psychology, vol. 67, No. 3, Sep. 1954, pp. 530-532.
Non-Final Office Action, Mailed Jan. 30, 2014, U.S. Appl. No. 13/521,217, filed Jul. 9, 2012, 41 pages.
Ocular Imaging Eye Model and Bracket, Ocular Instruments, Inc., 2005, 1 page.
Ophthalmic instruments—Optical coherence tomograph for the posterior segment of the human eye, ISO 16971, Apr. 15, 2015, 16 pages.
Rowe OCT Model Eye, Product No. 17019, Gulden Ophthalmics, 2021, 2 pages.
Thorlabs, Inc., LC4252-f = -30.0 mm, O1 UV Fused Silica Plano-Concave Lens, Uncoated, 1999-2021, 2 pages.
Wang et al., "A study of artificial eyes for the measurement of precision in eye-trackers," Behav Res., vol. 49, 2017, pp. 947-959.
Wang et al., "Model eye tool for retinal optical coherence tomography instrument calibration," Journal of Innovation Optical Health Sciences, vol. 14, No. 3, 2021, pp. 2150010-1 to 2150010-8.
Westheimer, Gerald, "The Maxwellian View," Vision Res, vol. 6, 1966, pp. 669-692.
Xie et al., "Application of 3-Dimensional Printing Technology to Construct an Eye Model for Fundus Viewing Study," PLOS One, vol. 9, Issue 11, Nov. 2014, pp. 1-9.

| SEGMENT | REGION | SUB-REGION | NAMED STRUCTURE | LAYER | INNER SURFACE | OUTER SURFACE |
|---|---|---|---|---|---|---|
| POSTERIOR CHAMBER | | | VITREOUS | | | |
| | INNER RETINA | GANGLION CELL COMPLEX | RETINAL NERVE FIBER LAYER | 1 | a | b |
| | | | GANGLION CELL LAYER | 2 | b | c |
| | | | INNER PLEXIFORM LAYER | 3 | c | d |
| | OUTER NUCLEAR LAYER | | INNER NUCLEAR LAYER | 4 | d | e |
| | OUTER RETINA | | OUTER PLEXIFORM LAYER | 5 | e | f |
| | | | OUTER NUCLEAR LAYER | 6 | f | h |
| | | | EXTERNAL LIMITING MEMBRANE | | | g |
| | | | OUTER SEGMENT | | | h |
| | | | ELLIPZOID ZONE | | | i |
| | | | RETINAL PIGMENT EPITHELIUM | | | j |
| | | | BRUCH'S MEBRANE | | | k |
| | CHOROID | | CHORIOCAPILARRIS | | | |
| | | | CHOROID | | | |
| | | | SCLERA | | | |

| VARIABLE | MEANING |
|---|---|
| N | NODAL POINT |
| O | CENTER OF CURVATURE OF THE POSTERIOR SPHERICAL SURFACE |
| P | POLE |
| h | TRUE POSTERIOR CHAMBER LENGTH |
| R | TRUE RADIUS OF CURVATURE OF POSTERIOR SPHERICAL SURFACE |
| $\theta$ | SCAN ANGLE (TRUE) |
| $\theta'$ | CENTRAL ANGLE OF POSTERIOR SPHERICAL SURFACE (TRUE) |
| $x, \Delta x$ | A DISTANCE AWAY FROM THE AXIS, MEASURED ALONG THE LINE TANGENT TO THE POSTERIOR SURFACE AT THE POLE (TRUE) |
| $y, y^*$ | SIMPLIFICATION OF NOTATION FOR $\Delta x + x$ (THAT IS, $y = \Delta x + x$ and $y^* = \Delta x^* + x^*$) |
| $s$ | AN ARC LENGTH ALONG THE POSTERIOR SPHERICAL SURFACE (TRUE) |
| $z, z_0$ | DIFFERENCE BETWEEN THE DISTANCE TO THE POSTERIOR SPHERICAL SURFACE AND THE DISTANCE TO THE REFERENCE ARM FROM THE NODAL POINT N ($z_0$ DENOTES THIS DIFFERENCE ALONG THE POLAR AXIS) |
| $h^*$ | ASSUMED POSTERIOR CHAMBER LENGTH (NOT CORRECT) |
| $\Phi$ | AZIMUTHAL ANGLE (TRUE) |
| $x^*, \Delta x^*$ | ESTIMATES OF $x$ AND $\Delta x$ CALCULATED USING THE ASSUMED BUT INCORRECT POSTERIOR CHAMBER LENGTH $h^*$ |
| $s^*$ | ESTIMATE OF $s$ CALCULATED USING $h^*$ |
| $\hat{z}, \hat{z}_0$ | DIFFERENCE BETWEEN THE DISTANCE TO THE POSTERIOR SPHERICAL SURFACE AND THE DISTANCE TO THE REFERENCE ARM FROM THE NODAL POINT, *AS MEASURED FROM THE TOP OF THE OCT B-SCAN TO THE IMAGE OF THE SURFACE* |
| $\Delta\theta$ | SMALL ANGLE THAT DEFINES THE LINE WIDTH OF EACH OF THE FIDUCIAL MARKINGS |
| $s_r, s_l$ | LOCATIONS OF THE LEFT AND RIGHT EDGES OF EACH MARKING ALONG THE POSTERIOR SPHERICAL SURFACE |
| $x_r, x_l$ | LOCATIONS OF THE LEFT AND RIGHT EDGES OF THE PROJECTION OF EACH MARKING ONTO THE HORIZONTAL PLANE |

SPECIFICATIONS OF THE ANALYTICAL EYE MODEL AND THE OPTOMECHANICAL EYE MODEL

| ANALYTICAL EYE MODEL | | | | |
|---|---|---|---|---|
| ELEMENT NO. | ELEMENT | RADIUS*(mm) | THICKNESS* (mm) | INDEX n** (550nm) |
| 1 | CORNEA | 7.87 | 0.574 | 1.376 |
| 2 | ANTERIOR CHAMBER | 6.40 | 3.520 | 1.336 |
| 3 | CRYSTALLINE LENS | 10.91 | 3.756 | 1.427 |
| 4 | VITREOUS CAVITY | -6.16 | 16.320 | 1.336 |
| 5 | RETINA | -13.00 | 0.250'' | 1.360 |
| OPTOMECHANICAL EYE MODEL | | | | |
| ELEMENT NO. | ELEMENT | RADIUS++(mm) | THICKNESS (mm) | INDEX n (550nm) |
| 1 | CORNEA | 10.3 | 3.98 | 1.519++ |
| 2 | ANTERIOR CHAMBER | INFINITY | 3.00 | 1.334+++ |
| 3 | CRYSTALLINE LENS | 30.360 | 2.590 | 1.519++ |
| 4 | VITREOUS CAVITY | -30.360 | 15.60 | 1.334+++ |
| 5 | RETINA | -13.00 | - | - |

*RADII AND THICKNESS OF THE ANALYTICAL MODEL ARE OBTAINED FROM DUBBELMAN FOR A RELAXED (OD ACCOMMODATION ADULT(35 YEARS) EYE[1-5]
--REFRACTIVE INDICES OF THE CORNEA AND OCULAR MEDIA IN THE ANALYTICAL MODEL ARE TAKEN FROM GULLSTRAND[1] EXCEPT FOR THE LENS FOR WHICH AN EQUIVALENT REFRACTIVE INDEX IS ADOPTED[7].
++RADII OF CURVATURE AND REFRACTIVE INDICES OF THE, GLASS LENSES (LA1074 AND LB1258, THORLABS)
+++REFRACTIVE INDEX OF BALANCED SALINE SOLUTION[8]

FIG. 14C

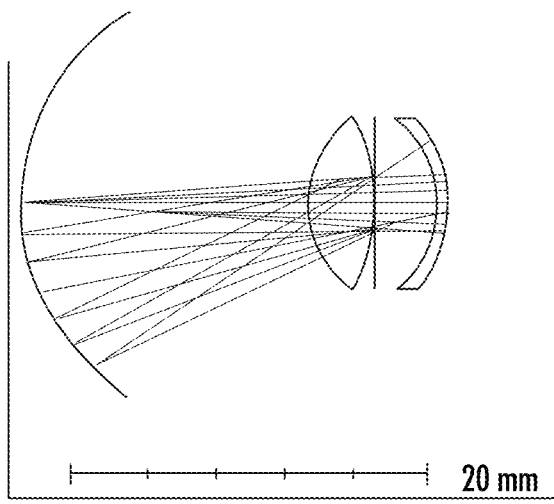

FIG. 14D

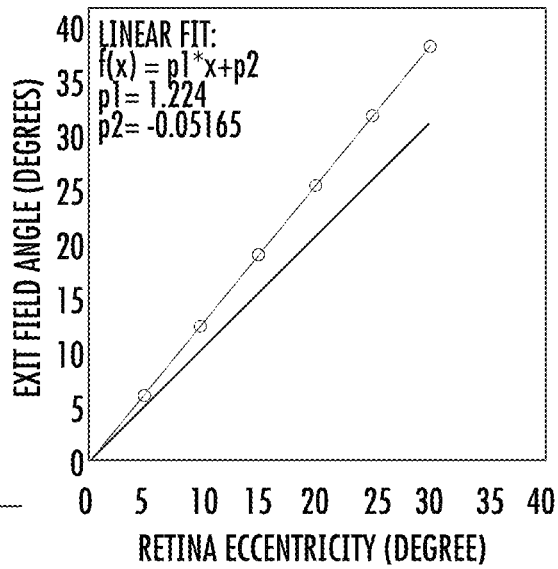

FIG. 14E

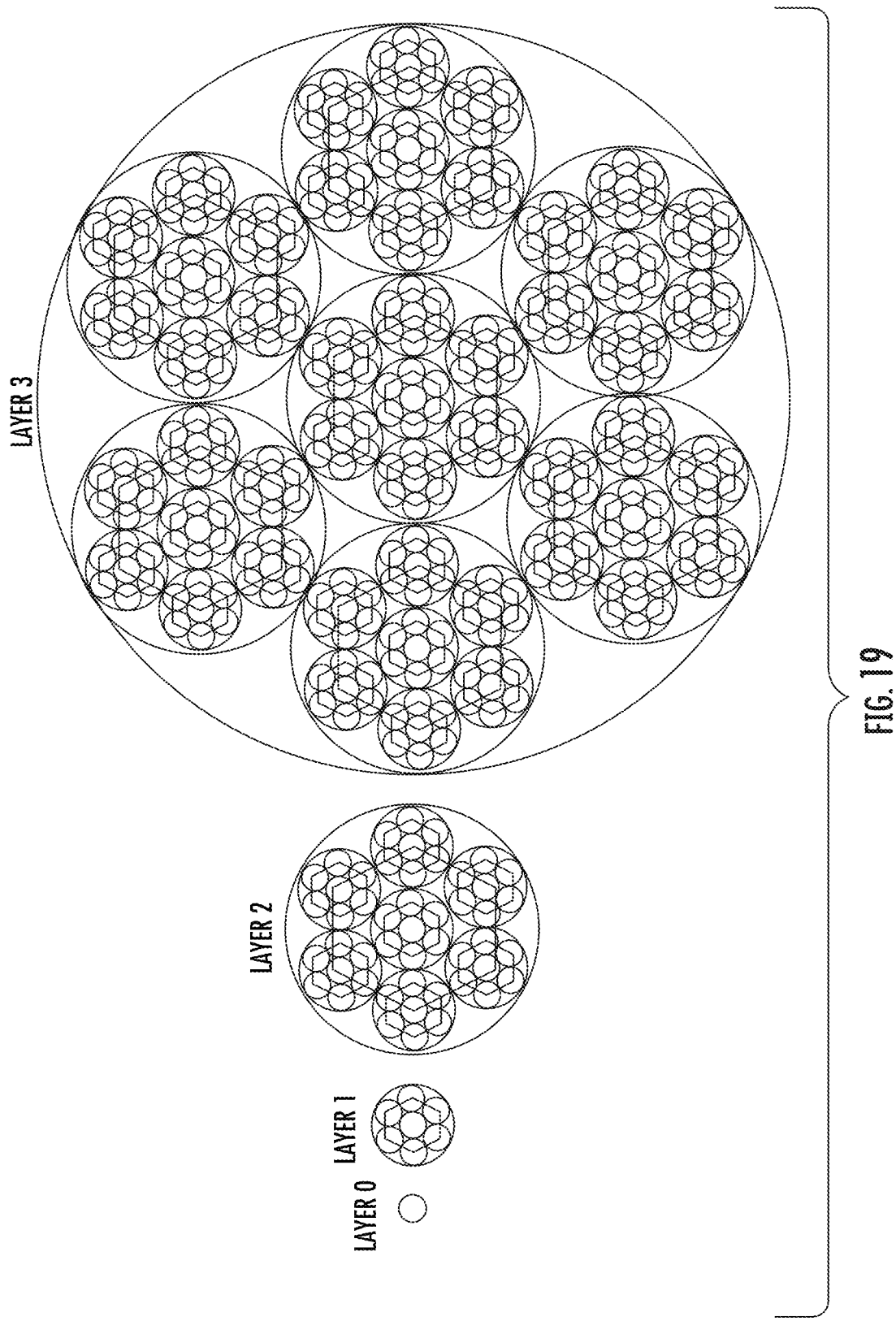

APPOLLONIAN
CIRCLE PACKING
(-1,2,2,3)

APPOLLONIAN
CIRCLE PACKING
(-6,11,14,15)

2300

| LAYER | THICKNESS (um) | ATTEN COEFF | ATTEN COEFF (dB/um) | LAYER ATTEN. (dB) |
|---|---|---|---|---|
| RNFL | 25 | 3 | -0.017 | -0.43 |
| GCC | 75 | 2 | -0.011 | -0.85 |
| INL | 25 | 1 | -0.006 | -0.14 |
| OPL | 25 | 2 | -0.011 | -0.28 |
| ONL (INNER) | 50 | 1 | -0.006 | -0.28 |
| ELM | 5 | 1 | -0.006 | -0.03 |
| ONL (OUTER) | 25 | 1 | -0.006 | -0.14 |
| OUTER RETINA | 50 | 3 | -0.017 | -0.85 |
| TOTAL | 280 | | | -3.01 |

APPARATUS FOR CALIBRATING RETINAL IMAGING SYSTEMS

CLAIM OF PRIORITY

The present application claims the benefit of and priority to U.S. Provisional Application No. 63/133,897, filed Jan. 5, 2021, entitled OCT Retina Systems and Calibration, the content of which is hereby incorporated herein by reference in its entirety.

GOVERNMENT CONTRACT

This inventive concept was made with government support under Grant No. EY031198 awarded by the National Institute of Health. The government has certain rights in the inventive concept.

BACKGROUND

Retinal imaging techniques are ubiquitous in optometry and ophthalmology. Retinal imaging is essential in the field of vision research, in the diagnosis and management of retinal disease, diabetes, and glaucoma, and in monitoring safety and effectiveness of new therapies in clinical trials. Increasingly, retinal imaging is applied to the study of neuromuscular disease, as the retina itself may be considered part of the central nervous system. In fact, the retina is connected to the major systems of the body and is a window to whole-body health.

The ever-increasing pressure on medical care demands improved patient outcomes at lower cost. Accurate diagnosis and prognosis of complex diseases, such as glaucoma and macular degeneration, require increasingly accurate and reproducible quantitative analysis of retinal images. The emergence of gene therapy for retinal disease is placing new demands on extracting objective outcome measures for specific therapies. Artificial Intelligence (AI)-assisted diagnostics generally require large volumes of consistent data to train images to observe disease-specific patterns more reproducibly than trained physicians/clinicians can do on their own.

Despite the criticality of retinal imaging in healthcare, there are few standards that guide quantitative analysis of retinal imaging. It is generally accepted that no two retinal imaging systems from different instrument manufacturers are considered truly interoperable. This is unfortunately specifically true in the space of optical coherence tomography (OCT). OCT produces three dimensional images of the retina in fine detail, and its use in the management of age-related macular degeneration (AMD) grew exponentially with the discovery of the mechanism for neovascularization in the retina and the release of a very effective class of treatments known as anti-VEGF in 2007. While OCT is very effective as an adjunct to the management of AMD, the glaucoma community continues to struggle to find similar effectiveness with OCT in the management of this disease.

To advance the effectiveness of retinal imaging and the discovery and validation of retinal imaging biomarkers, quantitative analysis of retinal images must become more accurate, more precise, and more reproducible. Specifically, retinal imaging systems must be calibrated with the precision of any laboratory instrument. Further, any two retinal imaging systems when equivalently calibrated should yield the same quantitative results when measuring the same patient under the same conditions.

Calibration of retinal imaging systems is challenging, not least because imaging the retina involves both the imaging device and the imaging optics of the patient: the cornea and lens form the lens of the ocular "camera" that focuses light from the imaging device to the retina "film plane," and this retinal "film plane" is uniquely shaped and located with respect to each patient's lens system. For historical reasons, OCT images are plotted along a cartesian axes representing a distance along the dimension of the retina. This spatial representation presumes a calibration from angle of view to length along the retina that is full of assumptions. Unlike a stopped clock that is correct twice a day, the current calibrated measures of a retina are almost never correct. Accordingly, improved calibration methods for retinal imaging systems are desired.

SUMMARY

Some embodiments of the present inventive concept provide a model eye for calibrating a retinal imaging system. The retinal imaging system includes a centered optical imaging system having first and second converging optical elements, an aperture stop of fixed or variable diameter D1 characterized by an optical axis, a nodal point, a focal plane, and a field of view ($2\theta$). The model eye includes a backplane having a negative radius of curvature R centered on the optical axis and a clear aperture diameter D2; a distance h along the optical axis from the nodal point to the backplane; an unobstructed field of view $2\theta$, where $\theta$ is an angle measured from the optical axis at the nodal point to an edge of the backplane at a radial limit of a clear aperture; a housing for enclosing elements of the model eye, the housing being a closed fluid fillable housing; a mechanical system for mounting, aligning, and preserving spacings of the elements of the model eye in the housings; and a pattern applied to the backplane, the pattern having a rotational symmetry and a radial repeating unit, extending substantially across the clear aperture, that spatially modulates intensity of light reflected from, or transmitted through, a surface of the backplane. In the model eye, D2/D1 is greater than 2, an absolute value of R/h is greater than 0.5, and $2\theta$ is greater than zero (0) degrees.

Further embodiments of the present inventive concept provide methods for recalibrating a retinal imaging device having an initial calibration, using a model eye having known structural parameters. The method includes imaging a model eye having a set of known parameters including a distance along an optical axis from the nodal point to a backplane of the model eye, a radius of curvature of the backplane of the model eye, and a position and dimensions of features patterned onto a surface of the backplane of model eye, with the Maxwellian-view retinal imaging device as initially calibrated to provide an image of the model eye; computing, from the image of the model eye, a new calibration function including known lateral coordinates of features on the model eye versus lateral coordinates reported by the retinal imaging system; deducing, from the new calibration function, an implied initial calibration function of the retinal imaging device; and providing a corrected calibration function to the retinal imaging device or applying a recalibration function to images acquired with the initial calibration of imaging device. At least one of the imaging, computing, deducing and providing are performed by at least one processor.

BRIEF DESCRIPTION OF THE DRAWINGS

FIG. 2C is a table defining physiological layers and surfaces of images and correspond to labels of FIGS. 2A and 2B according to some embodiments of the present inventive concept.

FIG. 13 is a table include definitions of variables used in equations in accordance with some embodiments of the present inventive concept.

FIG. 14C is a table detailing specifications of the analytical eye model and the optomechanical eye model of FIGS. 14A and 14B in accordance with some embodiments of the present inventive concept.

FIG. 14D is a diagram illustrating the focal characteristics of the analytical model eye, given a constant radius of curvature of 13.0 mm posterior to the double convex lens in accordance with some embodiments of the present inventive concept.

FIG. 14E is a diagram illustrating the correspondence between the external visual angle and the scan angle in terms of retina eccentricity in accordance with some embodiments of the present inventive concept.

FIG. 19 is a diagram illustrating the simplest representation of a hexlet, having the desirable properties that the circles are all "kissing" in accordance with some embodiments of the present inventive concept.

DETAILED DESCRIPTION OF EMBODIMENTS

Figure 1A:
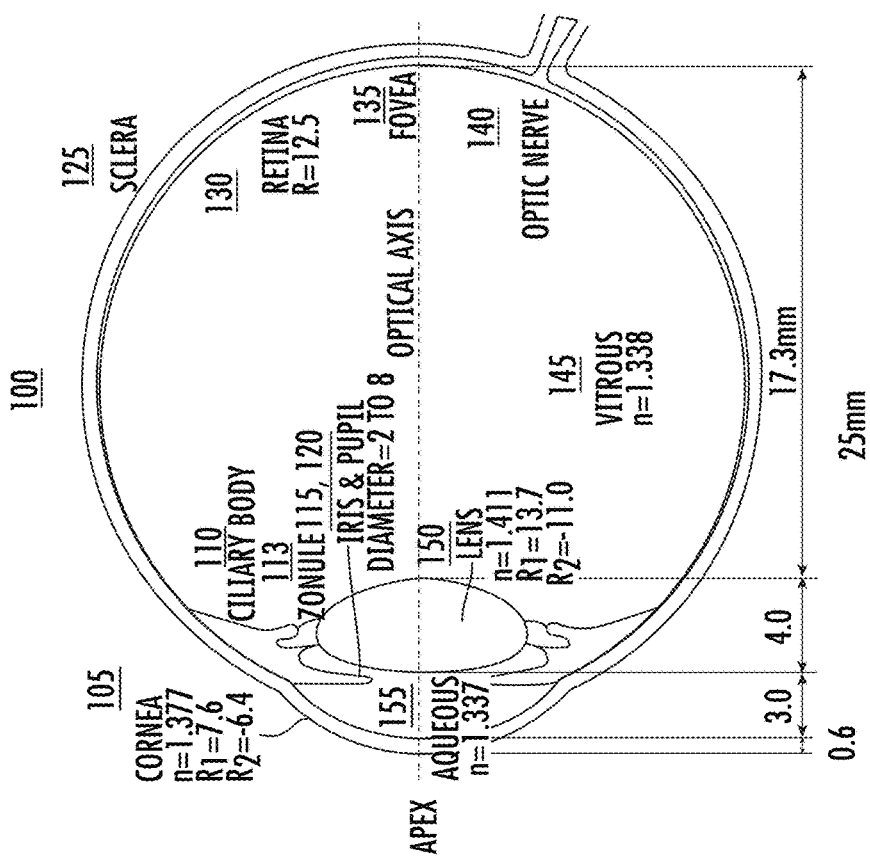
FIGS. 1A and 1B are diagrams illustrating model eyes.

The inventive concept now will be described more fully hereinafter with reference to the accompanying drawings, in which illustrative embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. Like numbers refer to like elements throughout. As used herein, the term "and/or" includes any and all combinations of one or more of the associated listed items. Similarly, as used herein, the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Reference will now be made in detail in various and alternative example embodiments and to the accompanying figures. Each example embodiment is provided by way of explanation, and not as a limitation. It will be apparent to those skilled in the art that modifications and variations can be made without departing from the scope or spirit of the disclosure and claims. For instance, features illustrated or described as part of one embodiment may be used in connection with another embodiment to yield a still further embodiment. Thus, it is intended that the present disclosure includes modifications and variations that come within the scope of the appended claims and their equivalents.

As discussed above, calibration of retinal imaging systems is challenging, not least because imaging the retina involves both the imaging device and the imaging optics of the patient: the cornea and lens form the lens of the ocular "camera" that focuses light from the imaging device to the retina "film plane," and this retinal "film plane" is uniquely shaped and located with respect to each patient's lens system. For historical reasons, optical coherence tomography (OCT) images are plotted along a cartesian axes representing a distance along the dimension of the retina. This spatial representation presumes a calibration from angle of view to length along the retina that is full of assumptions. Unlike a stopped clock that is correct twice a day, the current calibrated measures of a retina are almost never correct.

Thus, new calibration methods for retinal imaging systems, and particularly OCT imaging systems that incorporates an accurate calibration phantom with a limited amount of patient-specific ocular biometry is needed to improve the accuracy, reproducibility, and interoperability of retinal imaging systems, and enable the discovery of new generation of quantitative biomarkers for ocular and eye-related healthcare. Accordingly, some embodiments of the present inventive concept provide methods, systems and computer program products for calibrating or recalibrating imaging systems for imaging structures of the eye; a calibration module that allows for calibration of systems not specifically designed to account for the variability of the size of the eye; and methods for transforming images from one calibration set to another calibration set using the calibration module and subject-specific measurements of the eye.

As will be discussed, some embodiments of the present inventive concept further provide for a calibration apparatus and related methods that calibrate retinal imaging systems, specifically, "Maxwellian view" systems. A "Maxwellian view system" is a system that images (and/or illuminates) in a cone posterior to a pupil of limited aperture. The calibration apparatus of the present inventive concept may be a spherical model eye (SME) with a backplane having a defined posterior radius of curvature and a posterior chamber length, i.e. a distance from a pupil to the posterior pole of the model eye, with anterior focal optics, together which mimic the distances and relationships in the human eye as will be discussed further herein.

Figure 1B:
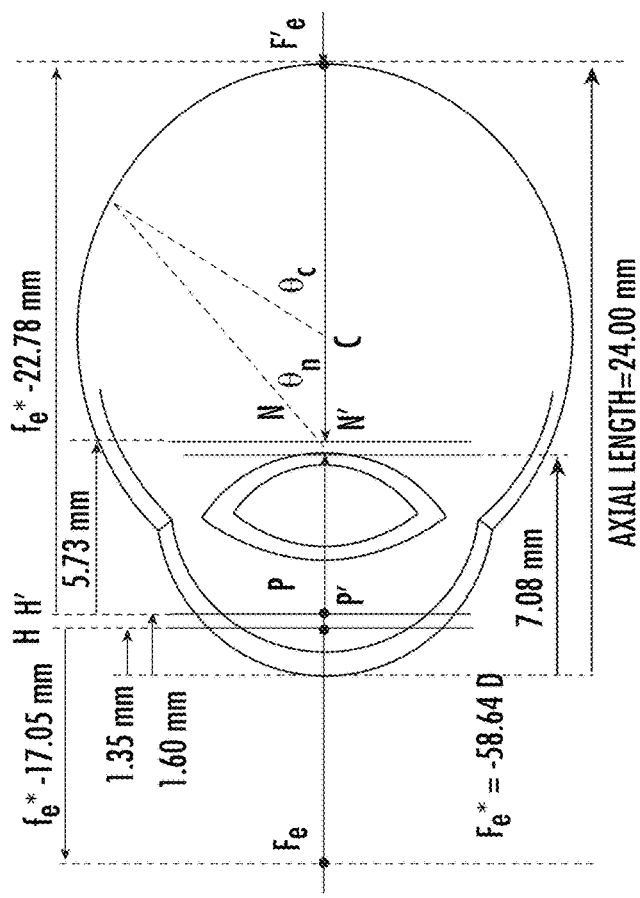

Referring to FIGS. 1A and 1B, diagrams of an eye illustrating the geometries important to retinal imaging will be discussed. Specifically, FIG. 1A illustrates a physiological model of the eye and FIG. 1B illustrates a reduced optical model of the eye. As illustrated in FIG. 1A, the model eye illustrates all portions of an actual eye and the associated measurements. In particular, FIG. 1A illustrates an anatomical model eye 100 including a cornea 105, a ciliary body 110, a zonule 113, an iris 115 that forms a pupil 120, a sclera 125, a retina 130, a fovea 135, an optic nerve 140, the vitreous 145, a lens 150 and the aqueous 155. It will be understood that the measurements provided in FIG. 1A are provided as examples of the anatomical model eye 100 only and that embodiments of the present inventive concept are not limited thereto.

As illustrated in FIG. 1B, the principal planes P and P' are the effective planes of refraction and the nodal points N and N' are the points from which rays appear to enter and exit the optical system at the same angles. The angle $\theta_N$ corresponds the angle of view to the retina that correlates to the visual angle of view. As is clear from FIG. 1B, the central angle $\theta_C$ measured from the center of curvature of the retina is always greater than $\theta_N$ because the posterior chamber length is greater than the radius of retinal curvature, which will be discussed further below.

Figure 2A:
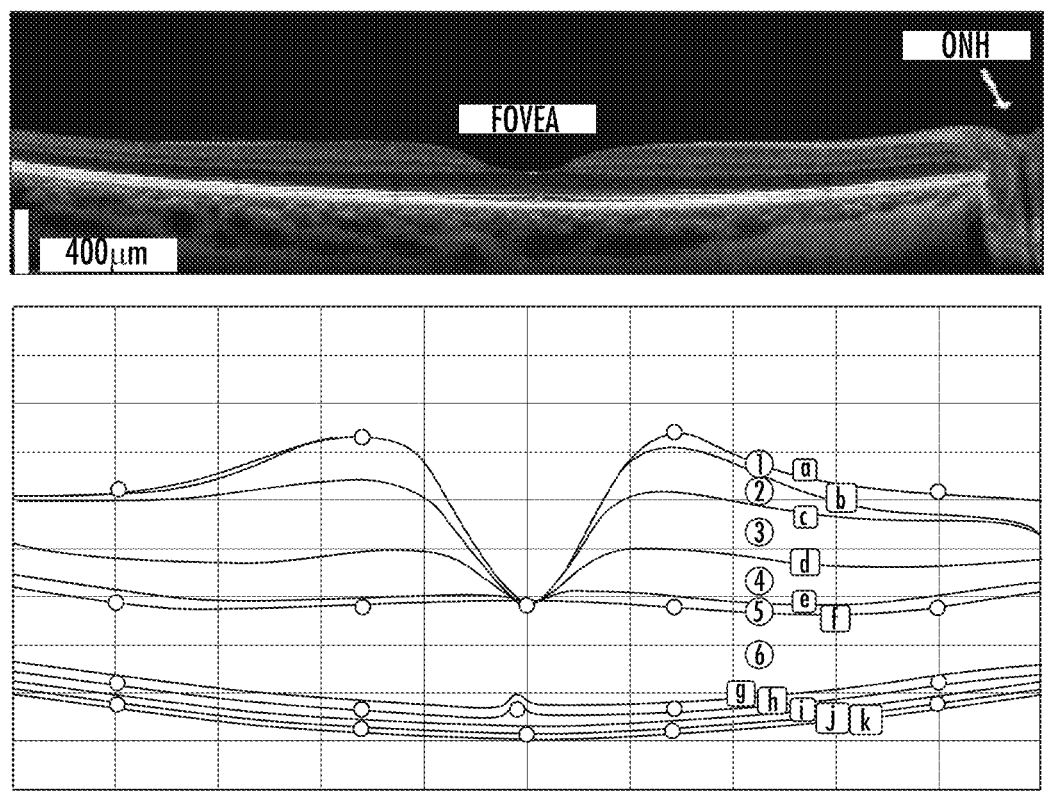
FIGS. 2A and 2B are graphs illustrating physiological structures of the retina centered on (A) foveal pit and (B) optic nerve head, respectively, in accordance with some embodiments of the present inventive concept.
Figure 2B:
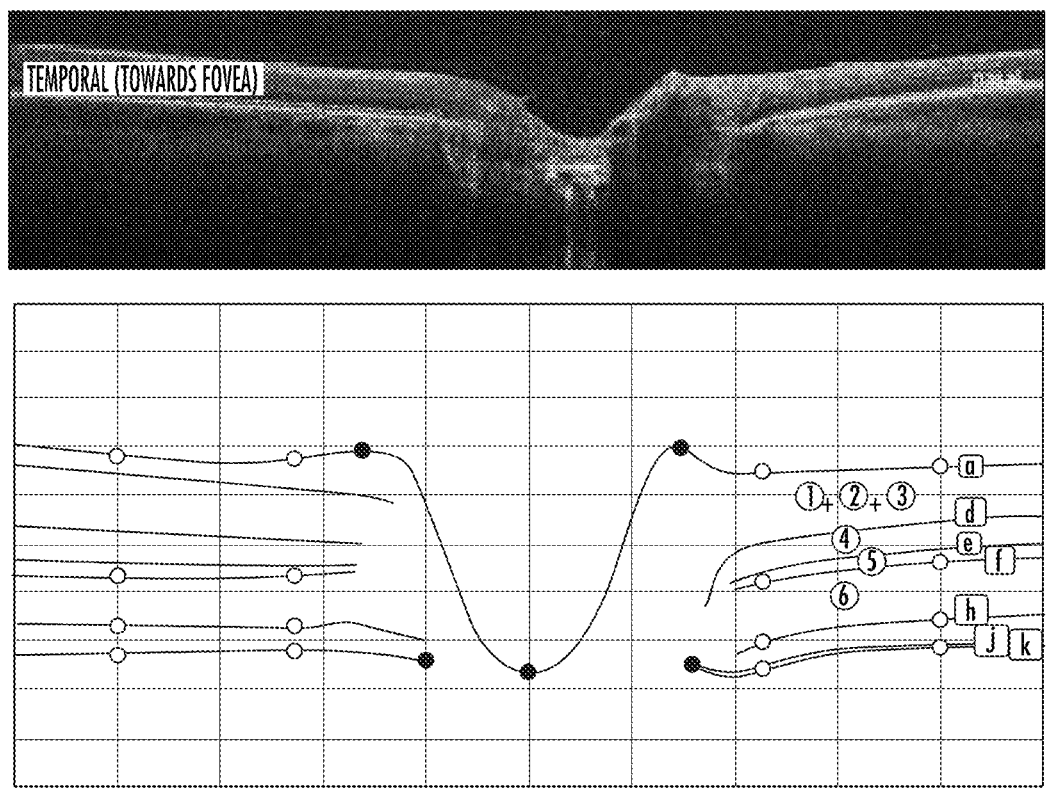

Referring now to FIGS. 2A and 2B, visualization and quantification of retinal structures will be discussed with respect to OCT cross sectional images of the retina. In particular, FIGS. 2A and 2B illustrate various layers and surfaces of the retina in the vicinity of the fovea (macula) (FIG. 2A) and in the vicinity of the optic nerve head (FIG. 2B). These structures carry generally accepted names, though as research advances, some of the naming conventions continue to evolve. The various layers of the retina are indicated by number-labeled filled circles (1-6) and boundary surfaces are indicated by alpha-labeled (a-f) and (a-k) open squares. The details with respect to the layers (1-6), inners boundary surfaces (a-k) and outer boundary surfaces (a-k) are provided in table 200 of FIG. 2C. As discussed above, some embodiments of the present inventive concept are focused on the retina. As illustrated in FIG. 1A, the retina 130 resides as the back surface of the posterior chamber of the eye. The structures of the retina are organized into the Inner Retina (adjacent the vitreous and facing the Anterior Segment (cornea and lens)) of the eye; the Outer Nuclear Layer (comprising the photoreceptors); and the Outer Retina. From the Vitreous to the Sclera, the layered structure of the retina as substantially visualized with OCT is listed in FIG. 2C. The numbered layers and alpha-labeled bounding surfaces are visible, amenable to manual segmentation and may be amendable to automated segmentation. Layers 2 and 3, the Ganglion Cell Layer and Inner Plexiform Layer, respectively, have soft, low contrast boundaries, and are for this reason often grouped as the Ganglion Cell Complex.

The (y, z) scales in the images of FIGS. 2A and 2B differ by an order magnitude. The total depth of view z in the images is less than 600 microns. The scan width y of the images is approximately 6 mm. The digital, or pixel resolution in a typical OCT image is 10 microns (y); 3 microns (z), and the optical resolution is closer to 20 microns (y); 6 microns (z). These values depend on specifics of a given imaging modality and specific technical implementations but illustrate the concept that precision calibrations in at least two orthogonal dimensions are generally required for quantitative analysis.

OCT calibrations in the depth direction z are a function of the wavelength and bandwidth of the optical radiation source in OCT, scaled by the refractive index of the subject. Lateral calibrations of OCT and similar retinal imaging systems are much more a function of the imaging optics and geometry of the specific eye under test.

Figure 3:
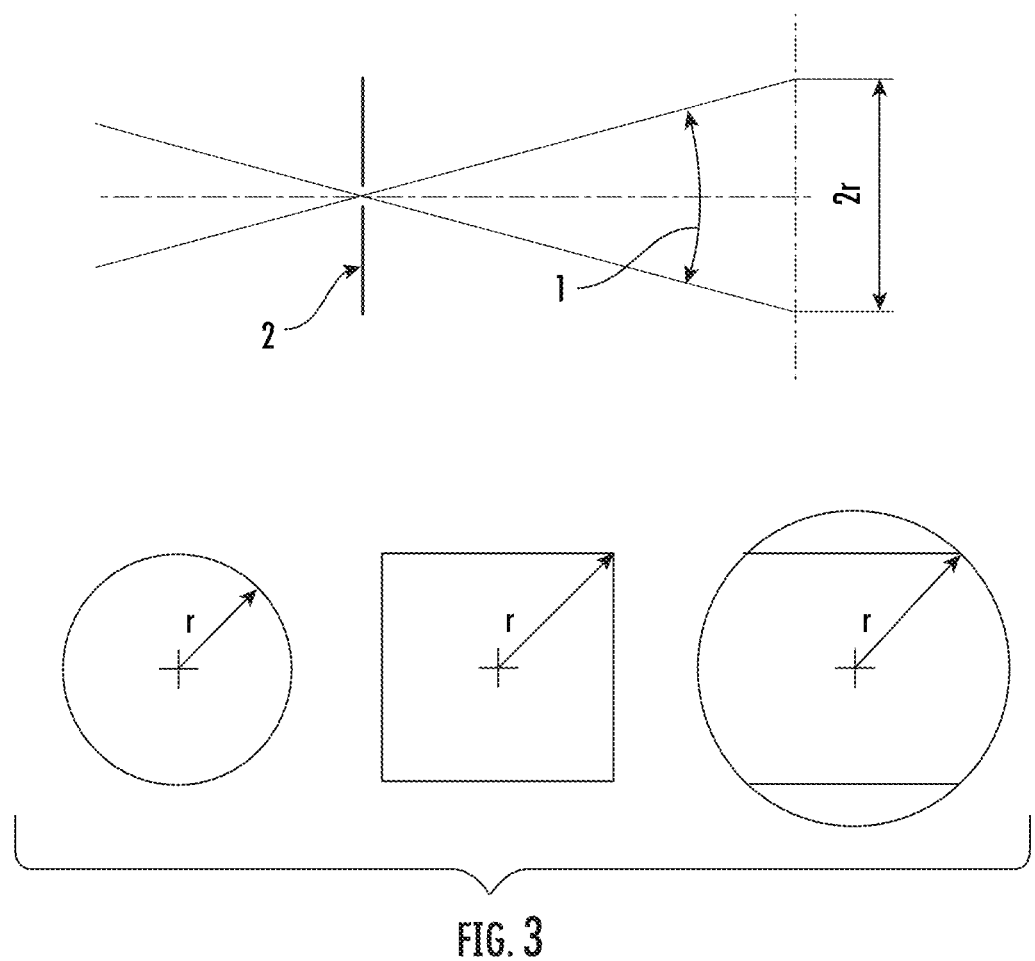
FIG. 3 illustrates a series of calibration diagrams illustrating a lateral distance r on a plane tangent to the optical axis at a distance of, for example, 17 mm from the exit pupil of a calibration artifact, according to ISO 16971.

A noticeable gap with respect to quantitative imaging of the retina is the lack of a meaningful calibration standard. ISO 16971 (*Ophthalmic instruments—Optical coherence tomograph for the posterior segment of the human eye*) is the only standard that defines lateral calibration of OCT systems. This standard specifies characterizing the field of view (FOV) of an OCT system by the angle that subtends a lateral distance r on a plane tangent to the optical axis at a specific distance of 17 mm from the exit pupil of a calibration artifact as illustrated in FIG. 3. This leads to well-known—and incorrect—results that the lateral distance measured in an image is r=17 tan θ. This result leads to incorrect scaling of Maxwellian view imaging system and, therefore, needs to be corrected: The imaged retina is not a plane but a surface of the locally-spherical eyeball; the value of 17 represents the nominal value of the adult posterior chamber length and needs adjustment for the specific patient under examination; and the retina has a radius of curvature that is always different from, and less than, this posterior chamber length. The implications of these details are discussed below.

Quantitative measurements of the retina depend directly on the length of the posterior chamber of the eye, which is an unknown at the time an imaging instrument is calibrated and is generally ignored in conventional commercial retinal imaging systems. Furthermore, the lack of meaningful standards has (a) made the quantitative application of adult OCT imaging systems to the under-developed eye of the child untenable; (b) has limited the clinical interoperability of imaging systems and their normative data to imaging systems of one model by one manufacturer; and (c) created a generation of retinal images that are simply inaccurate as they do not account for subject-specific ocular biometry. This lack of proper standards to provide a consistent and accurate set of calibration rules for retinal imaging systems dramatically increases the cost for introducing new instruments to the market and inhibits the development of new quantitative imaging biomarkers.

Accordingly, as discussed above, some embodiments of the present inventive concept provide a calibration apparatus and related method of use to improve quantitative retinal imaging independent of stage of development or intrinsic eye length, and to improve the interoperability of retinal imaging instruments to advance the development of new quantitative, objective imaging biomarkers for diagnosis and development of new ocular therapies.

Optics of the eye that will guide design of the Spherical Model Eye (SME) for Maxwellian-view retinal imaging systems will now be discussed. As illustrated in, for example, FIG. 1A, a typical adult eye has an axial length from apex (APEX) of cornea 105 to the fovea 135 of approximately 25 mm (24.00 in FIG. 2B). The imaging system of the eye is constructed of a cornea with an approximate focal power of +40 Diopter, a pupil that acts as an aperture stop, and a positive lens with an approximate focal power of +20 Diopter. As used herein, a "diopter" refers to a unit of refractive power that is equal to the reciprocal of the focal length (in meters) of a given lens. The nodal point of the eye (N,N'), shown, for example, in FIG. 1B, is the point from which distant rays appear to pass through the eye to the retina without deviation. The nodal point in the typical adult eye is behind the pupil, and nominally toward the back of the eye lens, and is not exactly at the exit pupil of the eye, but close. Embodiments of the present inventive concept uses exit pupil as that area that coincides with the conjugate of the scanning axis of a retinal imaging system and treats the nodal point as the axial location in the same plane for ease of exposition. The distance from the nodal point to the retina along the optical axis is approximately equal to the distance from the back surface of the eye lens to the retina, termed the posterior chamber length. The +60 Diopter combined optical power of the front of eye focus distant light rays to the retina at an approximate distance of 17 mm behind the lens, a nominal posterior chamber length in the adult eye.

The angular field of view of the adult eye is approximately equal in object space, what can be seen in front of the eye, and in image space, the angle subtended at the retina from the nodal point, with a slight correction from refraction at the cornea-air interface. The fovea 135 is the center of vision with the highest visual acuity. The FOV subtended by the fovea 135 is approximately 5 degrees. The broader region surrounding the fovea comprising the visual field is the macula, subtending approximately 20 degrees FOV. This is the extent of high visual acuity vision. Peripheral vision extends much wider, to approximately 120 degrees or more. Peripheral vision extends across the optic nerve head, which is the location of the well-known "blind spot." The entire observable region of the retina is called the "fundus." Disease progression that impacts vision in the macula causes the most concern for patients and clinicians. Diagnostic imaging systems may focus on a limited FOV, for example, to study the macular, or may target a wider FOV to observe the fundus more broadly. Increasingly, wider FOV systems are deployed to monitor disease progression from the periphery.

The radius of curvature "R" (e.g. FIG. 1A) of a typical adult eye is −13 mm, where the negative sign indicates curvature towards the front of the eye. As the posterior chamber length is greater than the radius of curvature of the retina, the angle subtended to a position on the retina from the point of view of the center of curvature will be greater than the angle to the same position on the retina from the point of view of the nodal point. This fact occasionally leads to some confusion if the imaging system designer reports the FOV of the imaging system from the perspective of the center of curvature of the retina. The value that more accurately aligns with the perceived FOV is the angle subtended from the nodal point of the eye.

Efficient imaging of the retina is accomplished with a Maxwellian-view imaging system. The exit pupil of a Maxwellian-view imaging system is designed to image to the entrance pupil of the eye. The entrance pupil is then conjugated to the exit pupil and focused on the retina. The entrance and exit pupil of the eye are nominally anterior to, and posterior to, the pupil, respectively. A Maxwellian-view imaging system provides the maximum radiant coupling efficiency with the minimum vignetting for projecting a source of optical radiant energy to the retina, or imaging from the retina. The angle of view of the Maxwellian-view system matches the optics of the eye, and thus is described by a conical expansion of the image from the exit pupil to retina.

Fundus photography, scanning laser ophthalmoscopes (SLO), and OCT are all examples of Maxwellian-view imaging systems. The term Fundus Photography is generally used for full field, flood-illuminated imaging systems. SLO and OCT are examples of scanning beam imaging systems in which the image is reconstructed from a scanned beam that maps out the image field sequentially. Parallelization may be applied so that an image is acquired by sequential linear arrays, as in line-scanning SLO (LSLO), and full field approaches are also utilized. In all cases, the imaging principles are generally the same.

OCT and SLO are both confocal scanning beam imaging systems. OCT captures a volumetric images, while SLO captures enface images only. Referring to OCT, it is useful to define some terminology.

As used herein, "A-scan" or "Amplitude Scan" refers to a axial array of image data along the optical ray of an OCT scan. An A-Scan provides information on signal intensity as a function of depth at a single lateral position of the retina. Similarly, "B-scan" refers to a two-dimensional image from a contiguous array of A-scans. A B-scan provides a cross-sectional view of the retina across a scanned path. A "C-scan" or "C-slice" refers to a two-dimensional enface view of a section of the retina, generally a plane orthogonal to the "B-scan." The primary image of an OCT image is generally a volume constructed of B-scans that are constructed of A-Scans. An enface view of an OCT image may be constructed from this volume with software post-processing. The primary image of an SLO is an enface view, or C-scan, of the retina. Lateral registration between OCT and SLO system is very direct, as the imaging and scanning geometries can be equal. In fact, many systems combine SLO sand OCT, at slightly different wavelengths, to capture the value of both modalities in a single acquisition. Similarly, many systems also incorporate fundus photography in a multimodal configuration, as the imaging geometries are both Maxwellian-view. Lateral calibration of any of these systems is directed by the same concepts.

As used herein, an OCT "enface" image is an orthogonal surface projection of an OCT volume for producing an (x,y) lateral array from a set of (z,y) cross-sectional B-scans. OCT "enface" images may be extracted for the entire depth of a retina or may be a more specific projection of specific retinal layers. The concept of en face, C-scan, and surface projection may be used interchangeably in the description of embodiments of the present inventive concept discussed herein.

As used herein, "subject" refers to the thing being imaged. It will be understood that although embodiments of the present inventive concept are discussed herein with respect to human eyes, embodiments of the present inventive concept are not limited to this configuration. The subject can be any subject, including a veterinary, cadaver study or human subject without departing from the scope of the present inventive concept. Additionally, aspects of the present inventive concept are applicable to many different types of collections of images, two-dimensional, three-dimensional, hyperspectral, video, and the like.

It is useful to understand how quantitative measurements that are important in retinal imaging. The retina is a complex layered structure whose observed features have been validated against histology. The characterization of the retina for use in automated or guided diagnostics and prognostics is quite challenging for the richness of the visual and neurological processes in sight. Certain measurements are established as standards of care and supported with normative data for the adult eye, yet the actual set of objective quantitative biomarkers that are extracted from volumetric images of the retina is quite slim, and largely limited to pathology of the mature adult retina. Use of the nerve fiber layer thickness is intended to support the diagnosis of glaucoma, but the diagnostic value remains fraught. Given the exceptional progress in understanding the visual processes and the development of therapies, including gene therapies that are successfully treating blindness, there is a clear need to develop and validate a more complete and robust set of imaging biomarkers to diagnose disease earlier, develop precision medical treatments, and screen patients as candidates for treatments. This problem is no less important for the pediatric population that have a lifetime of sight to consider.

Some embodiments of the present inventive provide for a methodology to increase the accuracy of existing and new retinal imaging systems, and to provide for cross-calibrating retinal imaging systems to improve interoperability of devices for precision quantitative research and clinical application.

Some embodiments of the present inventive concept utilize a model eye, for example, the model eye 100 discussed above. There are a variety of model eyes proposed or used in practice. The previous model eyes generally propose to address problems not directly related to system calibration, and therefore have various deficiencies with respect to their use of calibration.

An example of a model eye in commercial distribution is the Ocular Instruments, Inc. OEMI-7, shown as an assembled device in FIG. 4A and with engineering details in FIG. 4B. The device illustrated in FIGS. 4A and 4B device is a fair replica of the human eye, with an anterior chamber, a lens, and a fundus. Dimensions are specified in FIG. 4B including the total axial length of 25.8 mm, posterior chamber length of 18.4 mm, and radius of curvature of the retinal plane of 12 mm. The device illustrated in FIGS. 4A and 4B does not have fiducials designed to calibrate or otherwise provide reference to features as a function of scan angle that would be required for calibration. Rather, the conventional device is designed to "duplicate pathological problems found in the human eye." As stated by the manufacturer:

Model provides superior demonstration and training of common ophthalmic imaging devices. This eye model incorporates many useful features not available in other eye models, including a retinal detachment showing an elevated retina, a foreign body, optic disc, and blood vessels. In addition, fluorescent features within the eye allow simulated fluorescein imaging. A line at the 180° meridian designates the region of the equator.

Ocular Imaging Eye Model—Educational Aides—Products—Ocular Instruments (ocularinc.com)

Figure 4A:
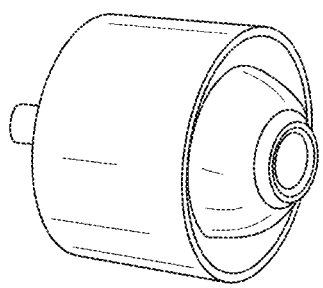
FIGS. 4A and 4B are diagrams illustrating a conventional a model eye in commercial distribution by Ocular Instruments, Inc. OEMI-7 and related engineering details, respectively.
Figure 4B:
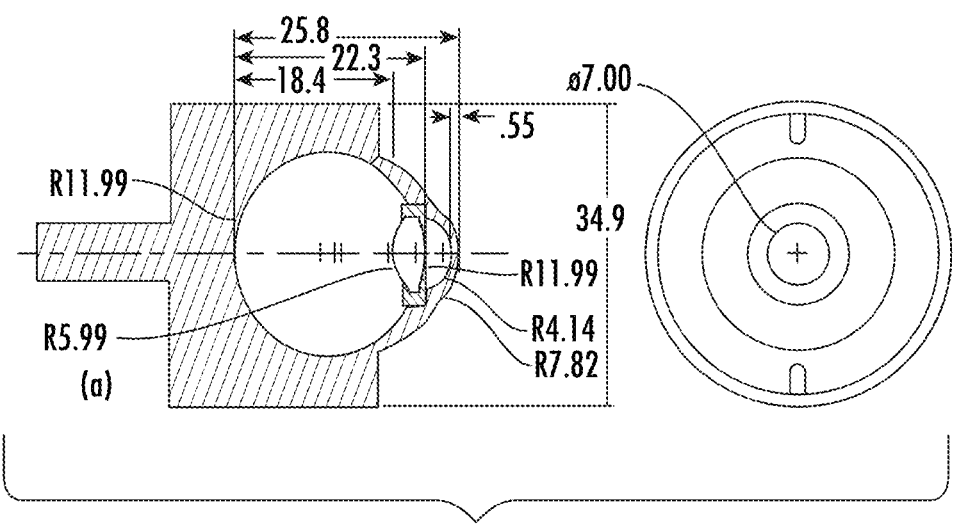

The OEMI-7 of FIGS. 4A and 4B has been used as a model to test lateral resolution on OCT imaging (Agrawal et al., *Characterizing the point spread function of retinal OCT devices with a model eye-based phantom*; Biomed Opt. Express. 2012 May 1; 3(5):1116-26), but this work was studying resolution of OCT systems as a function of imaging depth with additional features applied in the model eye and had nothing to do with scan calibration.

Another model eye in commercial distribution is the Rowe Model Eye sold by Gulden Ophthalmics as discussed in U.S. Pat. No. 8,440,230, the disclosure of which is incorporated herein by reference as if set forth in its entirety. As discussed therein, the model is also designed to replicate features of the retina, rather than to be used to calibrate an imaging system. In the case of the Rowe eye, layered structures at the retinal backplane are designed to appear as retinal layers, with a foveal dip and an optic nerve head. These layers are imposed on a flat backplane, though the benefit of a curved backplane is acknowledged. The objective of this model eye is to mimic ocular tissue as an ersatz sample when a living subject is not available, for example in training. This device is not designed to perform system calibration, and no indication is provided about how this device might be applied to calibration.

Figure 5A:
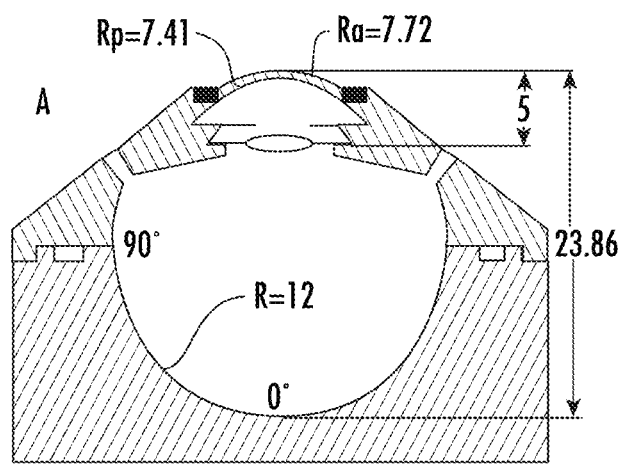
FIGS. 5A and 5B are a diagram and photo, respectively, of a 3D-printed model eye.
Figure 5B:
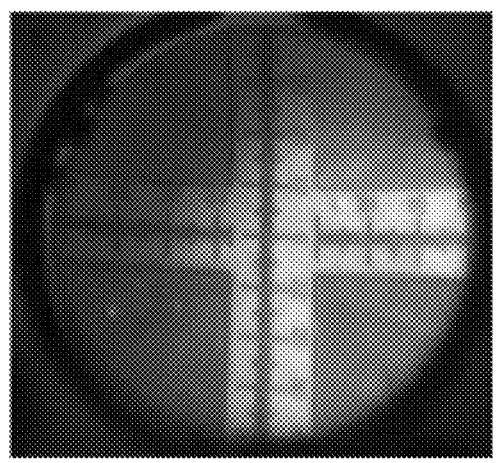

A three dimensional (3D) printed eye model of similar anatomical design has been described in *Application of 3-Dimensional Printing Technology to Construct an Eye Model for Fundus Viewing Study* by Xie et al. (2014). Xie emphasized the ability to 3D printed all structures of a model eye including the refractive surface and obtain good optical performance in imaging. The authors indicate some deficiencies of 3D printing the model eye, including feature resolution limited to 20 µm. The authors note that they have not evaluated the quality of such a device in actual imaging. This work advances the space for 3D printing refractive structures for a model eye but does not develop the art for calibration. A schematic for this device is illustrated in FIG. 5A and a photograph of the same is illustrated in FIG. 5B showing a cross-hair ruler inside the model.

Finally, another model eye proposed by Niven is discussed in U.S. Pat. No. 7,066,598, the disclosure of which is hereby incorporated herein by reference as if set forth in its entirety. Niven proposes a model eye with features focused on eliminating air bubbles in the visualization path of a fluid-filled cell. The specification of the patent makes brief reference to use in calibration, but there are no measurements or methods presented to how such calibration would be accomplished and, thus, Niven does nothing to overcome the ambiguities associated with under-specified calibration methods as discussed above.

Accordingly, some embodiments of the present inventive concept address the disadvantages discussed above with conventional systems and methods and overcome limitations of existing model eyes for use in precision calibration of Maxwellian-view imaging systems in general, Maxwellian-view retinal images specifically, and OCT, SLO and full-field fundus imaging system in particular as will be discussed further herein.

Some embodiments of the present inventive concept provide methods of calibrating systems using a model eye with known physical attributes, and incorporate certain known physical attributes of a subject, sample, or patient under test, and provide a rescaling of the original system calibration to provide a more accurately scaled image of the subject.

Some embodiments of the present inventive concept allow transformation of existing images on systems previously calibrated, by combining a new calibration on the original imaging system or suitably equivalent class of instrument with a known model eye as defined herein, obtaining a physical parameter of the subject of an existing image, and transforming an existing image such as to produce a new and more accurately scaled image of the subject retina.

A common scanning geometry of scanning beam retinal imaging systems relies on crossed-galvo mirror scanning to provide orthogonal directional scanning. This means that the exit pupil of a Maxwellian-view imaging system will be slightly different in the two orthogonal axes, and the scan calibration will also be slightly dependent on rotational angle about the optical access. Thus, embodiments of the present inventive concept provide for rotational angle calibration of devices.

Some embodiments of the present inventive concept provide a "calibration phantom" and method that allows for accurate cross calibration of retinal imaging devices. In the context of the present inventive concept, the term "calibration phantom" is used to enrich the concept of a "model eye" with the incorporation of appropriate internal structures, reticle, or fiducials and the like that provide accurate, precise, and reproducible measurements.

In addition to calibrating the scanning geometry of devices, it is desirable to calibrate the lateral resolution. Resolution of retinal imaging devices is a function of many factors of the imaging system, and of course of the optics of the subject. By holding the optics of the phantom constant, including an imaging backplane that is at the focal plane of the focal optics, the resolving capability of the imaging device can be isolated. Accordingly, some embodiments of the present inventive concept provide for measurement of the resolution of a retinal imaging system as a function of the scan angle.

OCT systems are volumetric imaging systems, providing depth-resolved visualization of retinal structures. Some embodiments of the present inventive concept provide an accurate and reproducible assessment of axial resolving power as function of depth through a multiplicity of layers as a function of scan position.

Further, optical radiation refracts at the interface between media of different refractive indices. This is well known and a significant factor in reconstructing images at the air-to-cornea interface. Refractive index changes in the posterior segment in the eye are much smaller, and the impact to imaging of refraction at the vitreous-retina interface is ignored. However, refraction is very much dependent on the angle of incidence of an optical ray at a refractive interface, and the angle of incidence is high at the edges of the fovea pit, in the optic nerve head, and the periphery of wide field retinal imaging systems. Accordingly, some embodiments of the present inventive concept provide a phantom that is suitable for quantifying the impact of refraction of quantitative thickness measurements of the retinal layers as a function of angle incidence.

Cartesian representation of retina and relation to a standard adult eye will now be discussed. As the description of Maxwellian-view imaging suggests, one might naturally plot an image of the retina in polar coordinates, correlated to the visual FOV. This is most often the case in traditional fundus photography, but for historical reasons this is not generally the case with scanning imaging systems. Instead, images are most often represented in cartesian coordinates, and lateral measurements are extracted from this cartesian representation. This leads to a very significant problem when accurate measurements are desired: the lateral measurements depend explicitly on the relationship between scan angle, axial distance of the posterior chamber, and relative curvature of the retina. The lateral scaling is by necessity different for every single individual, yet commercial imaging systems do not incorporate patient-specific biometry into their scaling equations.

Furthermore, the simplest scaling equation uses the trigonometric relationship between maximum scan angle, which is the parameter controlled by the imaging system, and the base and height of the triangle formed by the scanning beam. Not only is the height of the triangle not known for the individual subject, but because the retina is curved, the imputed distance to the retina from the center of the scan will be increasingly in error as the scan angle increases. The impact of this scaling technique for specific cases is examined herein using OCT as the reference imaging modality for convenience. It will be understood that embodiments of the present inventive concept are not limited to OCT and this method is used as an example only.

Case I: Nodal Point at Center of Curvature, Radius of Curvature R=h is Known

Figure 6:
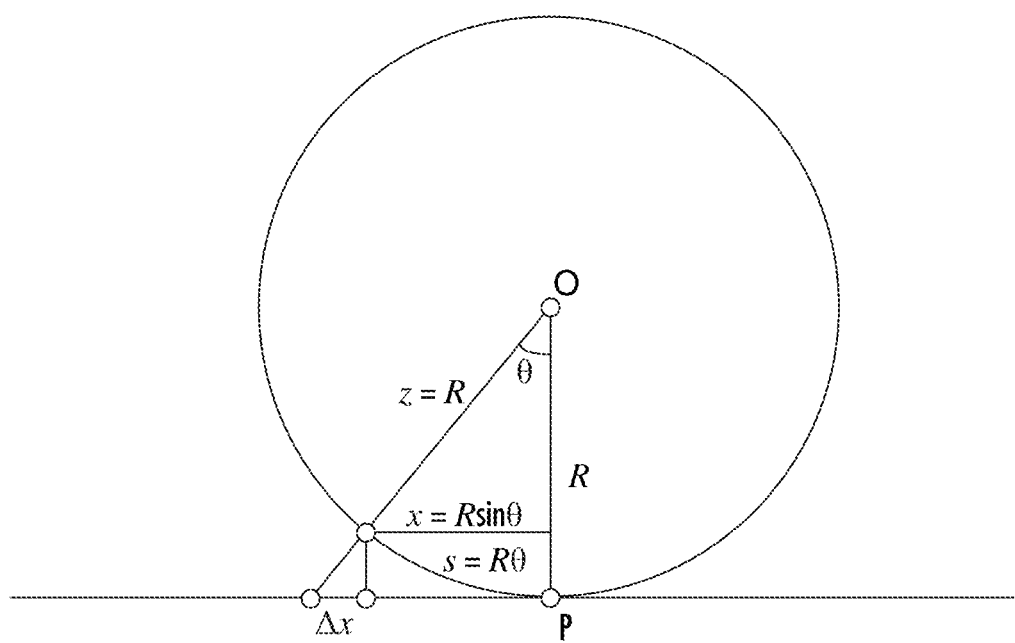
FIG. 6 is a diagram illustrating Case I. Nodal point at center of curvature, radius of curvature R=h is known in accordance with some embodiments of the present inventive concept.

Referring now to FIG. 6, assume that the sample/artifact being imaged is spherical having a radius R, and the nodal point corresponds to the center of curvature (O in FIG. 6), so that the axial distance h to the pole P is equal to the radius of curvature (this distance corresponds to the posterior chamber length from the nodal point to the fovea). The angle θ between the polar axis and each A-scan is known.

It can be assumed for this example that the z-coordinate of the surface for a given A-scan corresponds to the distance to the surface in the direction of θ as measured from the nodal point O, which is known to be the constant R in the case of a spherical artifact. Details of how the z-coordinate is actually calculated will be discussed below, but it does not matter for the case where the nodal point is coincident with the center of curvature.

Consider an OCT imaging system calibrated by setting a system scan angle to match a target lateral scan length, which is the normal process. Note that there are three lateral distances which become ambiguous in the absence of a clear standard for calibration. The path distance along the surface(s) is calculated as follows:

$$s=R\theta \qquad \text{Eqn. (1)}$$

where R is the radius of curvature and angle θ is the angle between the polar axis and each A-scan. The angle θ is controlled by the system and known. In an image, s is the physical distance of interest, and is only knowable in this example if the radius of curvature of the subject matches the nodal distance, this value is known, and the scan angle is known.

Potential ambiguities will now be discussed. The distance x of the position to the sample projected to the surface tangent to the pole is calculated as follows:

$$x=R \sin \theta \qquad \text{Eqn. (2)}$$

and this distance x is less than the actual distance along the surface of the sample: (x<s). The x-coordinate does not correspond to any real physical distance relative to the sample.

The horizontal distance along the ray drawn all the way to the tangent plane (see FIG. 6) is the distance x+Δx>s>x:

$$x+\Delta x=R \tan \theta \qquad \text{Eqn. (3)}$$

The error in the x-coordinate (Δx) would be calculated as follows:

$$\Delta x=R \tan \theta - R \sin \theta = R(\tan \theta - \sin \theta) \qquad \text{Eqn. (4)}$$

The radial direction from the center of curvature O is generally always perpendicular to the tangent to the surface at the scan's point of intersection. Therefore, one could argue that the correct x-coordinate is the arc length s as measured from the pole P, illustrated in FIG. 6. In these embodiments, the error in the computed value of x would be calculated as follows:

$$(x+\Delta x)-s=R \tan \theta - R\theta = R(\tan \theta - \theta) \qquad \text{Eqn. (5)}$$

Figure 7A:
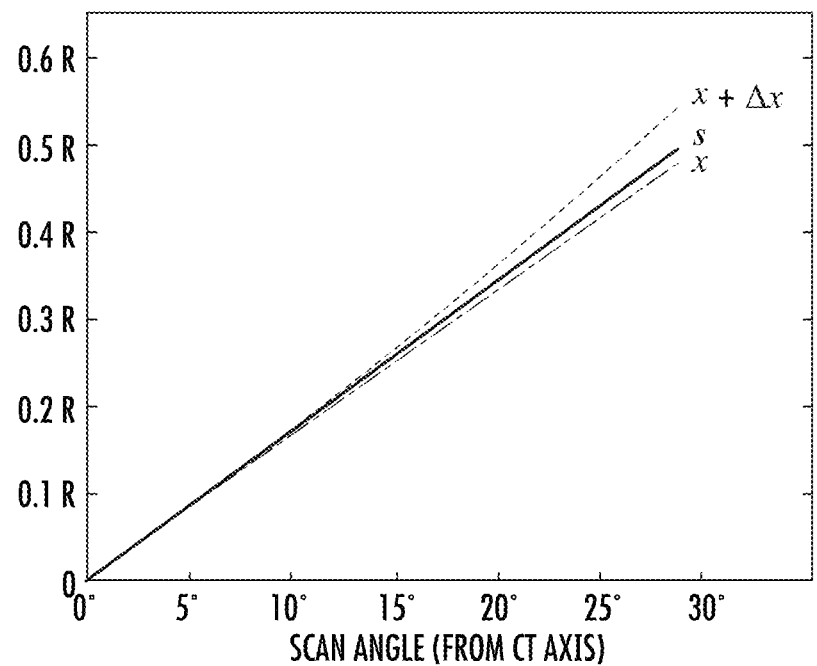
FIG. 7A is a graph illustrating values of x, s and x+Δx as a fraction of radius of curvature R versus angle from central axis (CT) in accordance with some embodiments of the present inventive concept.
Figure 7B:
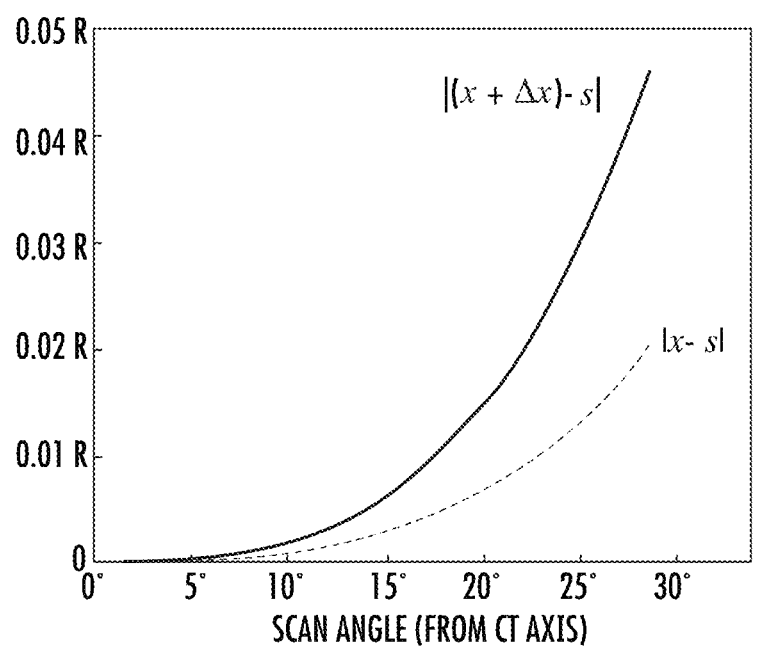
FIG. 7B is a graph illustrating the error between the two choices for projected distance x, and x+Δx and true surface path length s in accordance with some embodiments of the present inventive concept.

The values of x, s and x+Δx are plotted as a fraction of radius of curvature R versus angle from central axis (CT) in FIG. 7A. The relative error does not appear significant at shallow angles, which may explain why this error has been ignored. The error between the two choices for projected distance x, and x+Δx and true surface path length s are plotted in FIG. 7B. As illustrated, as precision quantification rises in importance and FOV increases, the relative error becomes non-trivial.

Case II: Nodal Point is at Center of Curvature, but System Calibrated Incorrectly Case II is substantially similar to Case I discussed above, except an incorrect value, h*, is used for calibration instead of the radius of curvature R. In this example, R is equal to the true posterior chamber length h. (This equality will be removed in the Case III discussed below). In other words, it is known that nodal point is at the center of curvature, but the OCT system is already set up to assume a particular value for the posterior chamber length that does not match the subject's radius of curvature.

Instead of the correct radius of curvature R=h, a value h*≠R is used to find the horizontal coordinate. In these embodiments, the error between each of the values computed in Case I and the actual arc length s is now calculated as follows:

$(x^*+\Delta x^*)-s=h^*\tan\theta-R$  Eqn. (6)

$x^*-s=h^*\sin\theta-R$  Eqn. (7)

$s^*-s=h^*\theta-R\theta=(h^*-R)$  Eqn. (8)

where starred (*) values refer to resultant values obtained when an incorrect value h* is used for the effective posterior scan length.

Figure 8:
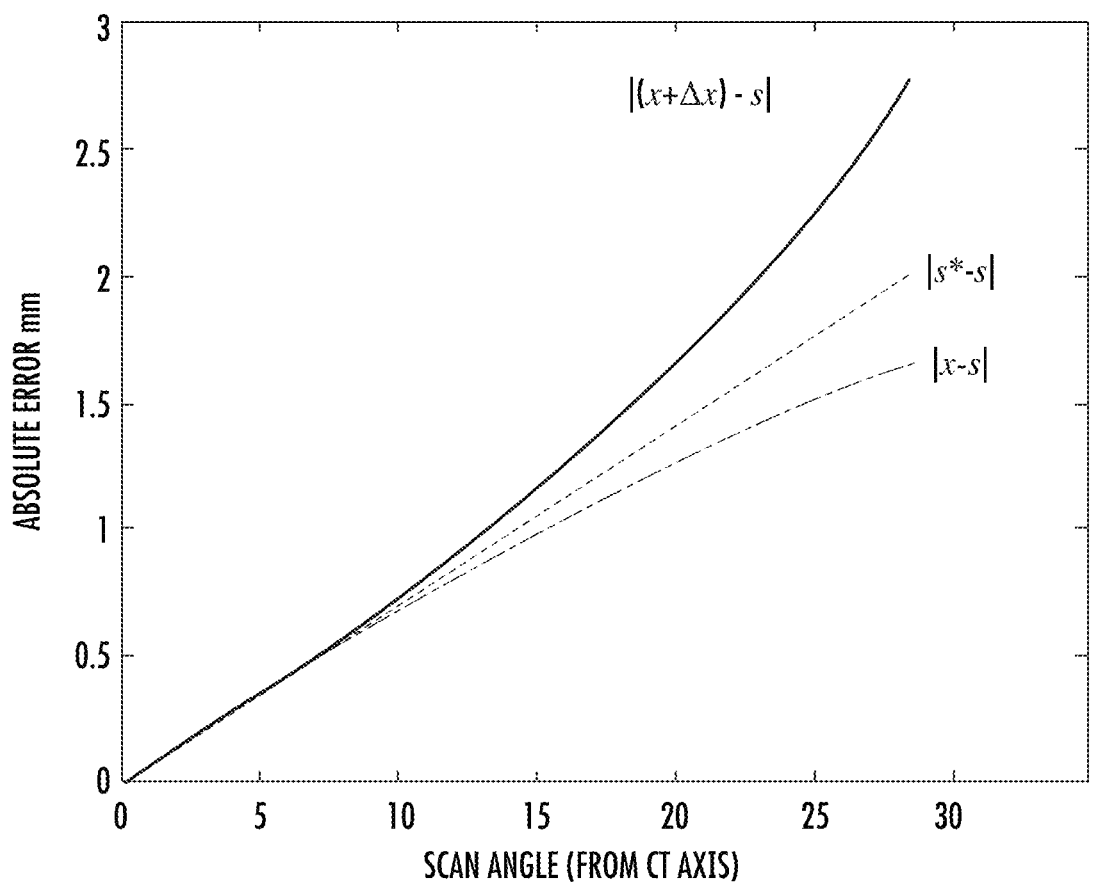
FIG. 8 is a graph illustrating absolute scan error in mm versus scan angle (from central axis CT) when R=h=17 mm in accordance with some embodiments of the present inventive concept.

Referring now to the graph of FIG. 8, the absolute error for each of these cases is illustrated as we move to a description of a calibration artifact as the subject, with physical values applied. In FIG. 8, when the radius of the spherical artifact is R=h=13 mm, it is assumed that an imaging system is calibrated for an assumed posterior chamber length to be h*=17 mm. It is noted that the error here is actually smaller when x is used as an estimate of the arc length s=Rθ than it is when the estimated arc length s*=h*θ is used. Resolving the ambiguity will lead to higher accuracy overall and better system interoperability, necessary for precision quantitative analysis.

Case III: Nodal Point N Lies on the Optical Axis but does not Coincide with the Center of Curvature O (that is, h>R). Both h and R are Known and Scan Equipment is Calibrated Correctly.

Figure 9A:
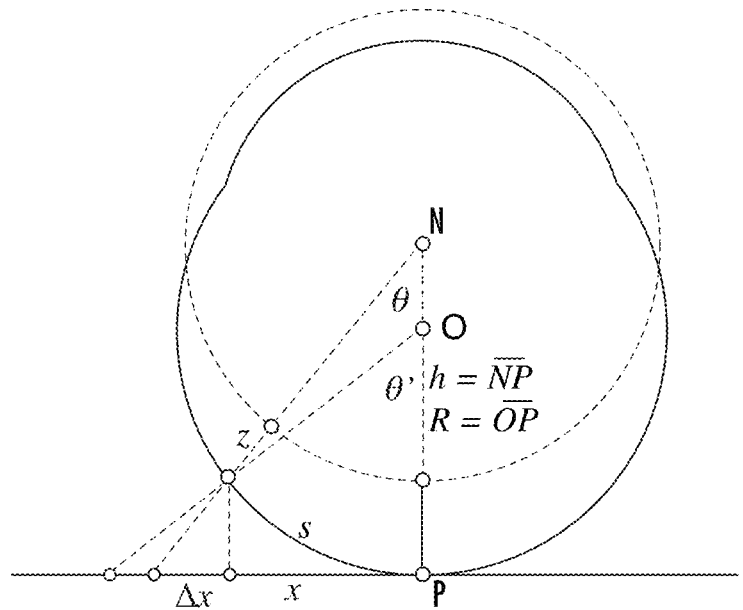
FIG. 9A illustrates a geometry of Case III where a Nodal point N lies on the optical axis but does not coincide with the center of curvature O (that is, h>R) in accordance with some embodiments of the present inventive concept.

In embodiments associated with Case III, both the radius of curvature R of the posterior surface as well as the posterior chamber length h are known from the nodal point to the pole, and these two distances are not the same. The geometry of Case III is illustrated in FIG. 9A.

As in Case I, x+Δx=h tan θ. However, in Case III the scan angle θ is not a central angle, so x itself cannot be immediately obtained, and the arc length s is not directly proportional to θ. Instead, the central angle is denoted θ' and it is noted that x=R sin θ' and s=Rθ'. It will be understood that the nodal angle is a known angle and is controlled by the imaging system.

Figure 9B:
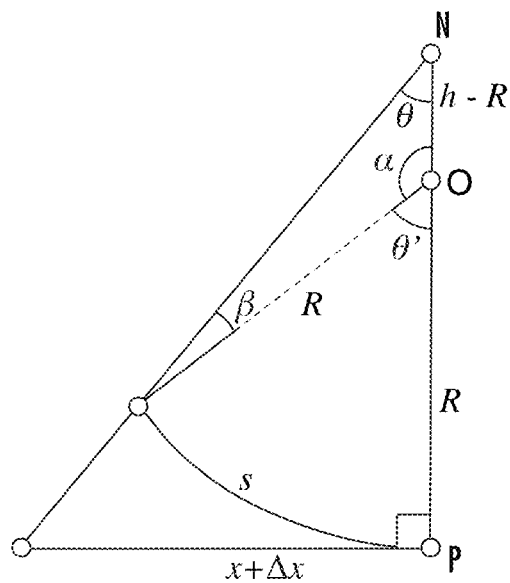
FIG. 9B is a diagram illustrating relationships between variables for Case III in accordance with some embodiments of the present inventive concept.

To find the central angle, the following relationships illustrated in FIG. 9B are noted. As is clear from FIG. 9B, α+θ'=180° and θ+α+β=180°. Therefore, the angle β can be written in terms of the known angle θ and the unknown central angle θ' is calculated as follows:

$\beta=\theta'-\theta$  Eqn. (9)

Using the law of sines, the relationship may be obtained as follows:

$\dfrac{\sin\theta}{R}=\dfrac{\sin(\theta'-\theta)}{h-R} \Rightarrow \left(\dfrac{h-R}{R}\right)\sin\theta=\sin(\theta'-\theta)$  Eqn. (10)

which can be solved for the central angle θ':

$\theta'=\theta+\sin^{-1}\left(\dfrac{h-R}{R}\sin\theta\right)$  Eqn. (11)

Since 0<R<h and 0<θ<90°, the argument of the arcsine function is positive and therefore θ'>θ, which is expected. Finally, the correct arc length s, as well as the value x, can be written in terms of the scan angle and other known parameters as follows:

$s=R\theta'=R\theta+R\sin^{-1}\left(\dfrac{h-R}{R}\sin\theta\right)$  Eqn. (12)

and $x=R\sin\theta'=R\sin\left(\theta+\sin^{-1}\left(\dfrac{h-R}{R}\sin\theta\right)\right)$  Eqn. (13)

$=R\sin\theta\sqrt{1-\left(\dfrac{h-R}{R}\sin\theta\right)^2}+(h-R)\sin\theta\cos\theta$ $=\sin\theta\sqrt{R^2-(h-R)^2\sin^2\theta}+\dfrac{1}{2}(h-R)\sin 2\theta$ Note that x+Δx=h tan θ does not depend on the central angle or the radius of curvature of the artifact.

Figure 9C:
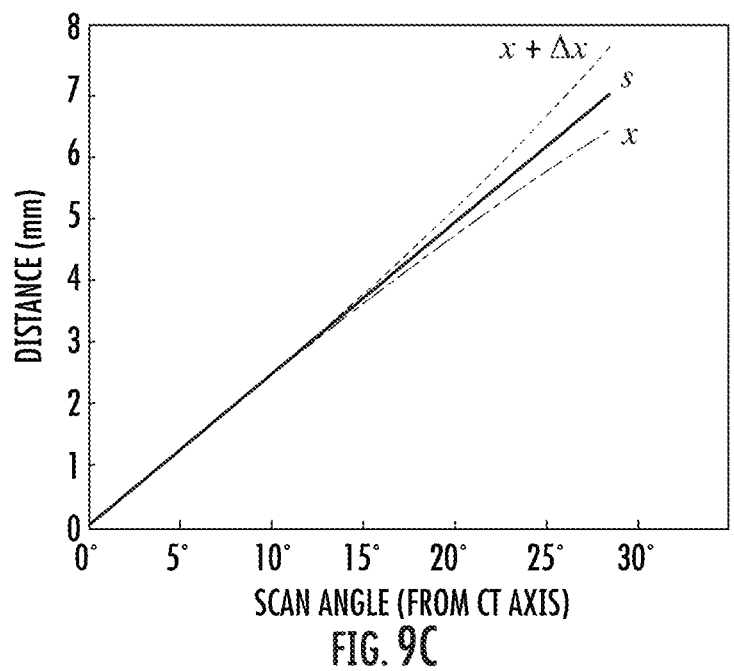
FIGS. 9C and 9D are graphs illustrating the different measures of distance from the pole P as a function of the scan angle θ when the radius of curvature of the artifact is R=10 mm but the axial distance from the nodal point to P is h=14 mm in accordance with some embodiments of the present inventive concept.
Figure 9D:
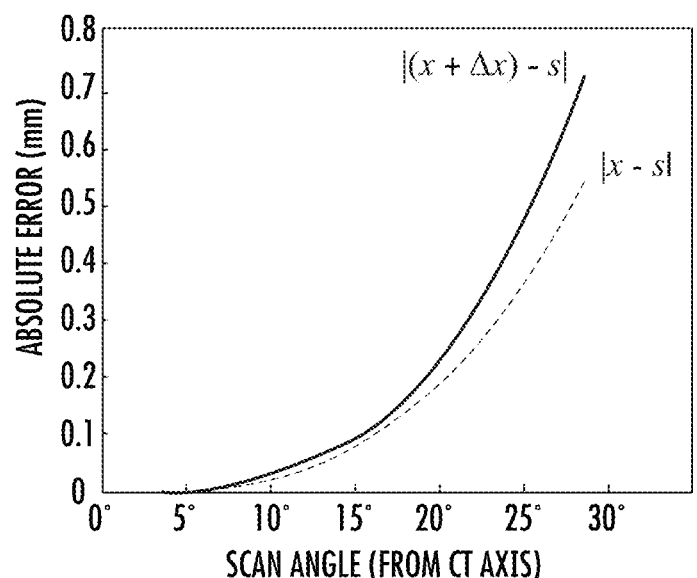

FIGS. 9C and 9D illustrate the different measures of distance from the pole P as a function of the scan angle θ when the radius of curvature of the artifact is R=10 mm but the axial distance from the nodal point to P is h=14 mm. These values are consistent with the dimensions of a pediatric eye, for example younger than about 2 years of age. FIG. 9C is a graph illustrating the absolute distances versus scan angle θ. FIG. 9D is a graph illustrating the error in the trigonometric estimates x and x+Δx from the distance measured along the surface s.

Design and Application of a Model Eye to Calibration

Application of these various geometries to specification of a calibration phantom, methods to calibrate or recalibrate a Maxwellian-view retinal imaging or projection system, and methods to correct by transformation an imaged acquired with a first calibration method, using the proposed calibration phantom and known physical attributes of a particular subject's eye will be discussed.

For purposes of the present specification, examples directed to OCT imaging will be discussed, as OCT introduces the depth dimension that is useful in fully explaining calibration procedures for Maxwellian-view systems. However, it will be understood that embodiments of the present inventive concept are not limited to OCT systems. Any results not explicitly dependent on a value z in the following is extensible to any other Maxwellian-view system.

In OCT imaging, scanned beams of light are directed to the sample, for example, a retina or the surface of a calibration phantom, and backscattered or reflected radiation is interfered with a reference light to obtain the signal that becomes the OCT image. The A-scan of an OCT image is directly aligned to the optical ray path and is the result of beam propagation including any interface refractions. Thus, an A-scan i is a column of an image in z at a point $y_i$. That column appears linear in OCT space but may have followed a refracted path. The units of z in an OCT image are units of length, for example, microns or millimeters. The units of $y_i$ are less clear and must be specified and calibrated. The imaging systems control an angle θ, but in OCT and SLO images, as discussed, the displayed units are typically specified as length.

The z-coordinate of each A-scan does not actually correspond to the distance from the nodal point, but rather from a point of equal optical path length difference (OPLD) between the reference path and sample path of the imaging system. Each OCT image is constrained to a window dictated by other parameters of the OCT technology, with a specific reference surface of constant OPLD. In a well-designed Maxwellian-view optical system, the surface of equal OPLD will be a circle—or sphere in three dimensions—around the exit pupil, e.g., the conjugate of the scanning axis of the system.

Figure 10A:
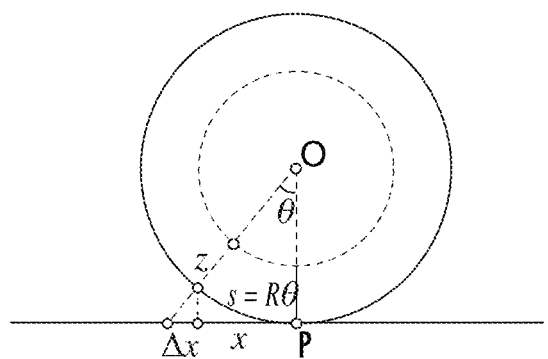
FIGS. 10A through 10C are diagrams illustrating optical path length difference z in various geometries in accordance with some embodiments of the present inventive concept.

The apparent surface of an uncorrected OCT image of a retina or a calibration phantom will be a measure of the distance of the subject surface from the surface of constant OPLD. In FIG. 10A, an arbitrarily defined circle of constant OPLD centered on the center of curvature (nodal point and center of curvature are collocated) for the case where we image a circle (or sphere from the center of curvature) is provided. The distance $z(\theta)$ in this case is a constant, for example, the surface of the image is a straight line (in 2D) or a plane (in 3D).

The image swept out by the imaging system has a depth of focus (DOF) defined at the focal surface, and with respect to OCT, a depth of view, defined by the coherence-gated imaging window. The OCT imaging window depth $z_{max}$ is of the order 3 mm (a design parameter that may be significantly greater or somewhat less) and much broader than the depth of focus; the following discussion is made with respect to OCT but relevant to other Maxwellian view imaging systems.

Figure 11A:
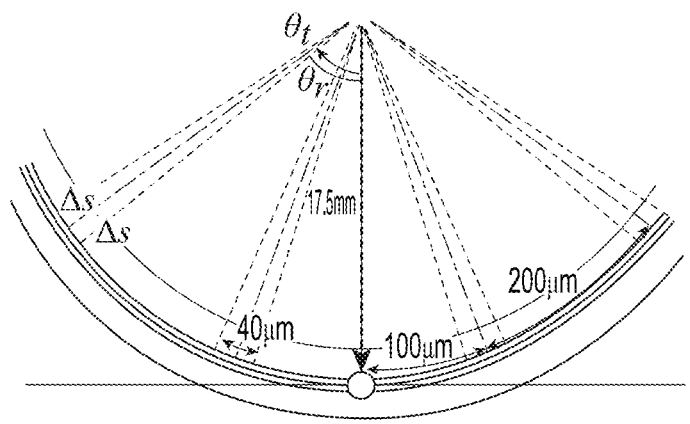
FIG. 11A through 11C are diagrams illustrating details of OCT imaging windows in accordance with some embodiments of the present inventive concept.
Figure 11B:
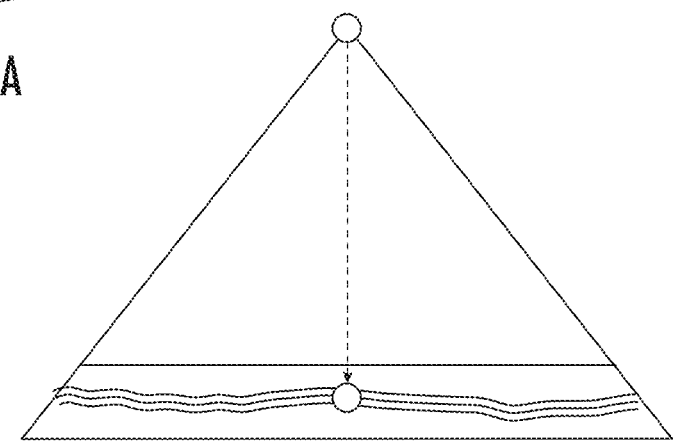

By optical construction, the exit pupil of the anterior optics of the eye, the area from which the retinal image is conjugated for return to the imaging system, is a region of constant OPLD. This is approximately, if not precisely, co-planar with the nodal point. The top and bottom of an OCT image window are also by construction surfaces of constant OPLD. The top and bottom of the OCT windows are at increasing radii perpendicular to the rays sweeping angularly from the nodal point, as shown in FIG. 11A. The lateral width of the OCT window is the arc length of the circle swept by the scan, and therefore the lateral dimension, or width $w_{scan}^{top}=(2\theta)*(\pi/180)*h^{top}$ and $w_{scan}^{bottom}=(2\theta)*(\pi/180)*h^{bottom}$ which are not the same, as illustrated in FIG. 11B. For an adult eye of h=17 mm and an OCT window depth $z_{max}$=3 mm, $w_{scan}^{top}=(0.84)*w_{scan}^{bottom}$. This is a property of Maxwellian view, and is not observed in telecentric imaging, for example, of the anterior segment with OCT.

Figure 10B:
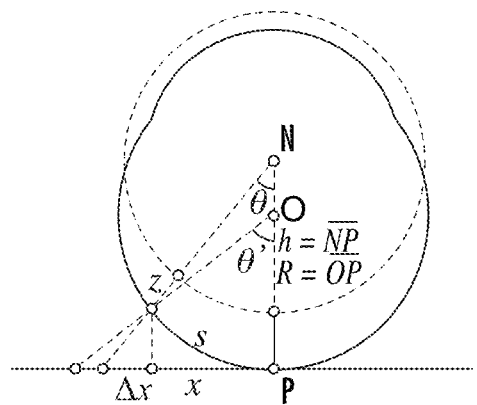

In a more general case of an eye or an appropriately constructed phantom, the radii of curvatures of the surface of constant OPLD and the imaged surface will not be equal, and surface of the image $z=f(\theta)$ will not be a constant. In fact, the image of surface will also not be equivalent to the actual shape of the surface; this fact is obvious from FIG. 10B. However, with a properly calibrated device, where the surface of constant OPLD is knowable, in principle, the image for the surface of constant OPLD may be corrected.

Figure 10C:
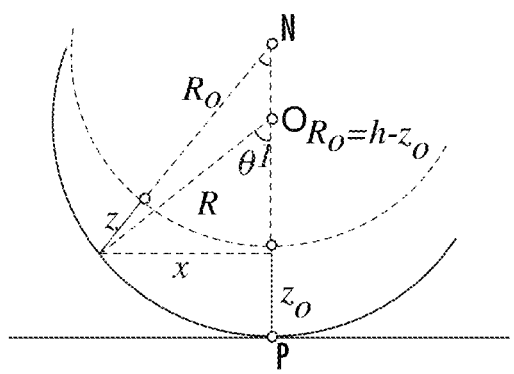

Referring to FIG. 10C, a relationship between the parameters h, R, and $\theta$ and the scan data points z can be derived. Recall that z is the difference between the distance to the surface and the distance to the reference arm, which is modeled as a circle of unknown radius $R_0$ centered at N (as shown in the FIG. 10A). Since it is known that $\overline{NP}$=h and $\overline{OP}$=R, $R_0$ can be determined in terms of the difference between the posterior chamber length h and the measured distance $z_0$ to the pole. Thus, the total distance from the nodal point to an arbitrary point on the posterior surface can be represented by the following equation:

$$R_0+z=h-z_0+z. \qquad \text{Eqn. (14)}$$

Note that this distance forms the hypotenuse of a right triangle with base x opposite scan angle $\theta$. This base is shared by the right triangle using the central angle $\theta'$, thus:

$$x=R\sin\theta'=(h-z_0+z)\sin\theta \qquad \text{Eqn. (15)}$$

Finally, with some substitution and rearrangement, a formula for z as a function of $\theta$ in terms of h, R, and the measured value $z_0$ is as follows:

$$(h-z_0+z)\sin\theta = R\sin\left(\theta+\sin^{-1}\left(\frac{h-R}{R}\sin\theta\right)\right) = \qquad \text{Eqn. (16)}$$

$$R\sin\theta\sqrt{1-\left(\frac{h-R}{R}\sin\theta\right)^2} + (h-R)\sin\theta\cos\theta$$

And therefore, $$z = z_0 + R\left(\sqrt{1-\left(\frac{h-R}{R}\sin\theta\right)^2} - \cos\theta\right) - h(1-\cos\theta) \qquad \text{Eqn. (17)}$$

Given a known artifact (calibration phantom), this equation can now be solved for the unknown scan angle $\theta$ in terms of the known artifact parameters h and R and the value $z_0-z$ obtained from the B-scan, where $z_0-z$ is distance from the surface of constant OPLD to the surface of the subject in the image as follows:

$$h-(z_0-z) = R\sqrt{1-\left(\frac{h-R}{R}\sin\theta\right)^2} + \qquad \text{Eqn. (18)}$$

$$(h-R)\cos\theta \Rightarrow \frac{h-(z_0-z)}{R} - \frac{h-R}{R}\cos\theta =$$

$$\sqrt{1-\left(\frac{h-R}{R}\sin\theta\right)^2} \Rightarrow 1-\left(\frac{h-R}{R}\sin\theta\right)^2 =$$

$$\left(\frac{h-(z_0-z)}{R} - \frac{h-R}{R}\cos\theta\right)^2 = \left(\frac{h-(z_0-z)}{R}\right)^2 -$$

$$2\frac{(h-(z_0-z))(h-R)\cos\theta}{R^2} + \left(\frac{h-R}{R}\cos\theta\right)^2$$

$$\frac{(h-(z_0-z))^2 - 2(h-(z_0-z))(h-R)\cos\theta}{R^2} =$$

$$1-\left(\left(\frac{h-R}{R}\sin\theta\right)^2 + \left(\frac{h-R}{R}\cos\theta\right)^2\right) =$$

$$\frac{R^2-(h-R)^2}{R^2} \Rightarrow h^2 - h(z_0-z+R) + \frac{1}{2}(z_0-z)^2 =$$

$$(h-(z_0-z))(h-R)\cos\theta \Rightarrow \cos\theta =$$

$$\frac{\frac{1}{2}(z_0-z)^2 - h(z_0-z+R) + h^2}{(h-(z_0-z))(h-R)}$$

And therefore, the scan angle and surface sag $z_0-z$ of the image are directly related by:

$$\Rightarrow \theta = \cos^{-1}\left(\frac{\frac{1}{2}(z_0-z)^2 - h(z_0-z+R) + h^2}{(h-(z_0-z))(h-R)}\right) \qquad \text{Eqn. (19)}$$

Thus, with a properly constructed calibration phantom where the nodal distance $\overline{NP}$=h and the radius of curvature $\overline{OP}$=R of the surface, or backplane of the phantom, can be controlled, the angular scan of an (OCT) imaging system can be calibrated simply by analyzing the surface sag of the image of the calibration phantom.

Unfortunately, the assumptions for $\overline{NP}$=h and $\overline{OP}$=R used in calibrating imaging systems are neither standardized nor reported. A value of $\overline{NP}$=h is implied to plot an angular scan along a cartesian axis. The value is generally assumed to that of a typical adult (systems are measured against each other to achieve similar, but not precisely equivalent scales), and may or may not be consistent with ISO 16971. The lateral scaling is not referenced to a curvature R of the retina, but assumes a trigonometric projection as described above. Further, any implied h is necessarily wrong in the case of any specific subject. Therefore, a way to recalibrate an imaging system, extract the implied value of h* and provide a transformation to rescale images according to a correct calibration and correction for the specific eye length (specifically posterior chamber length) of the subject is needed. Case IV: Nodal Point N Lies on the CT Axis with h>R, R is Known, but the Value h* is Used in Place of the True Distance h from the Nodal Point to the Pole P.

Embodiments of the present inventive concept relate to Case IV are substantially similar to those discussed above with respect to Case III, but the imaging system is designed to assume that an axial distance h*≠h. For a given imaged calibration phantom (model eye) with posterior chamber length h, we have the following errors:

$$(x^* + \Delta x^*) - s = \qquad \text{Eqn. (20)}$$
$$h^* \tan\theta - R\theta' = h^* \tan\theta - R \sin^{-1}\left(\frac{h-R}{R}\sin\theta\right)$$

$$x^* - s = R \sin^*(\theta') - R\theta' \qquad \text{Eqn. (21)}$$
$$= R \sin\theta \sqrt{1 - \left(\frac{h^*-R}{R}\sin\theta\right)^2} +$$
$$(h^* - R)\sin\theta\cos\theta - R\sin^{-1}\left(\frac{h-R}{R}\sin\theta\right)$$

$$s^* - s = \left(R\sin^{-1}\left(\frac{h^*-R}{R}\sin\theta\right)\right) - \left(R\sin^{-1}\left(\frac{h-R}{R}\sin\theta\right)\right) \qquad \text{Eqn. (22)}$$
$$= R\left(\sin^{-1}\left(\frac{h^*-R}{R}\sin\theta\right) - \sin^{-1}\left(\frac{h-R}{R}\sin\theta\right)\right)$$

the errors in x+Δx and x due to just the mis-calibration of h are:

$$(x^* + \Delta x^*) - (x + \Delta x) = (h^* - h)\tan\theta \qquad \text{Eqn. (23)}$$

$$x^* - x = R\sin\theta\sqrt{1 - \left(\frac{h^*-R}{R}\sin\theta\right)^2} + \qquad \text{Eqn. (24)}$$
$$(h^* - R)\sin\theta\cos\theta - R\sin\theta\sqrt{1 - \left(\frac{h-R}{R}\sin\theta\right)^2} -$$
$$(h - R)\sin\theta\cos\theta$$
$$= R\sin\theta\left(\sqrt{1 - \left(\frac{h^*-R}{R}\sin\theta\right)^2} - \sqrt{1 - \left(\frac{h-R}{R}\sin\theta\right)^2}\right) + (h^* - h)\sin\theta\cos\theta$$

The variables used in these equations are defined in the table 1300 of FIG. 13.

Figure 12A:
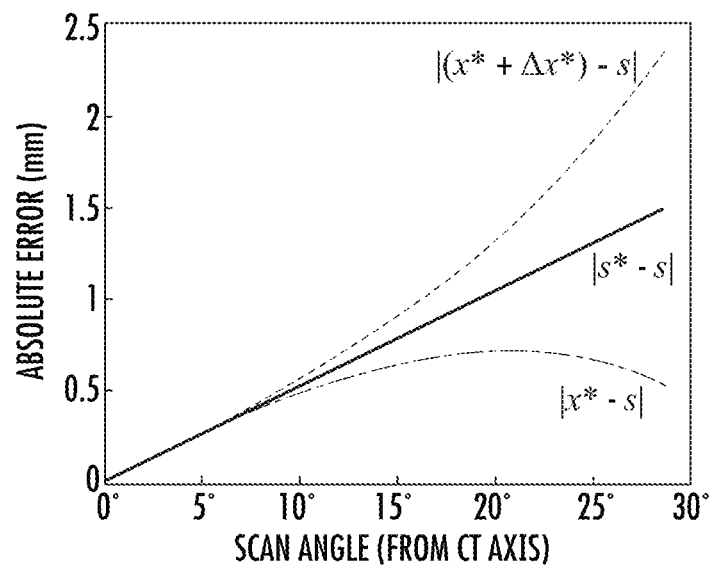
FIGS. 12A and 12B are graphs illustrating various errors if R=10 mm and h=14 mm in accordance with some embodiments of the present inventive concept.
Figure 12B:
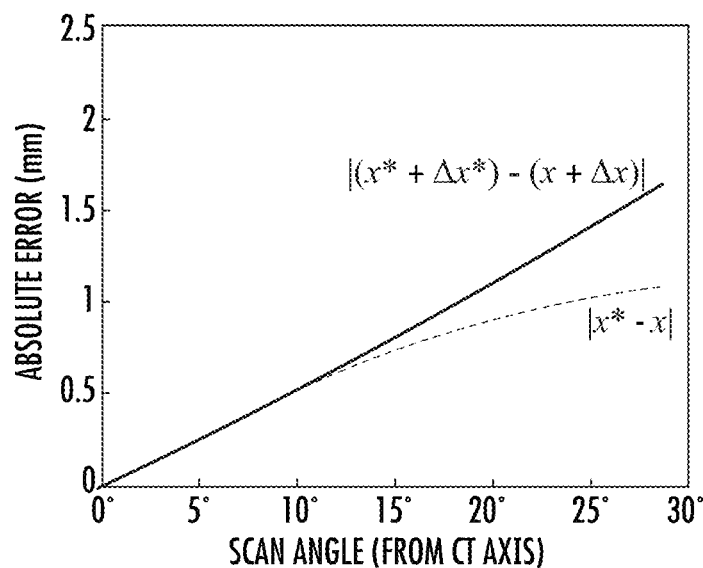
Figure 12C:
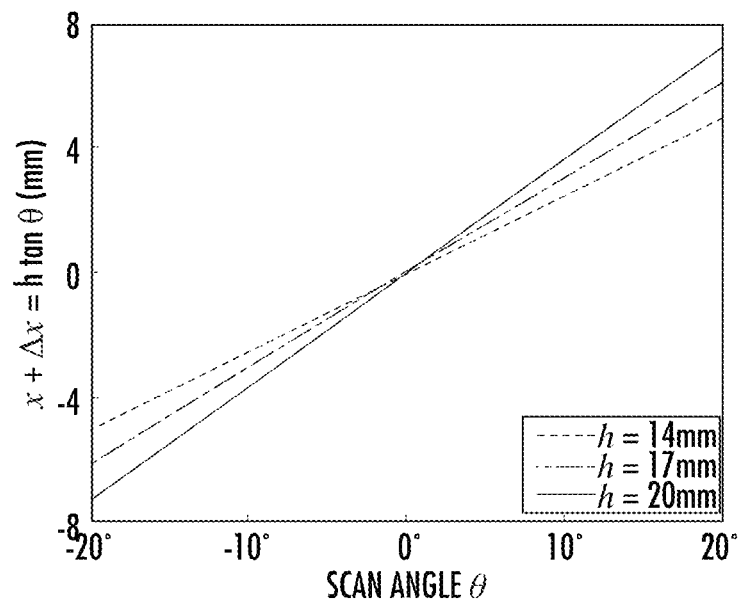
FIG. 12C is a graph illustrating the imputed scan length h tan θ versus scan angle when the calibration assumption h*=17 and the true posterior chamber length is 3 mm shorter or longer: h=14 mm or h=20 mm in accordance with some embodiments of the present inventive concept.

FIGS. 12A and 12B illustrate the various errors if R=10 mm and h=14 mm but the OCT scanner is configured to use h*=17 mm. The case of imaging a pediatric eye with a system calibrated for the adult eye. The ocular biometry of a subject is a variable. FIG. 12C illustrates the imputed scan length h tan θ versus scan angle when the calibration assumption h*=17 and the true posterior chamber length is 3 mm shorter or longer: h=14 mm or h=20 mm.

Figure 12D:
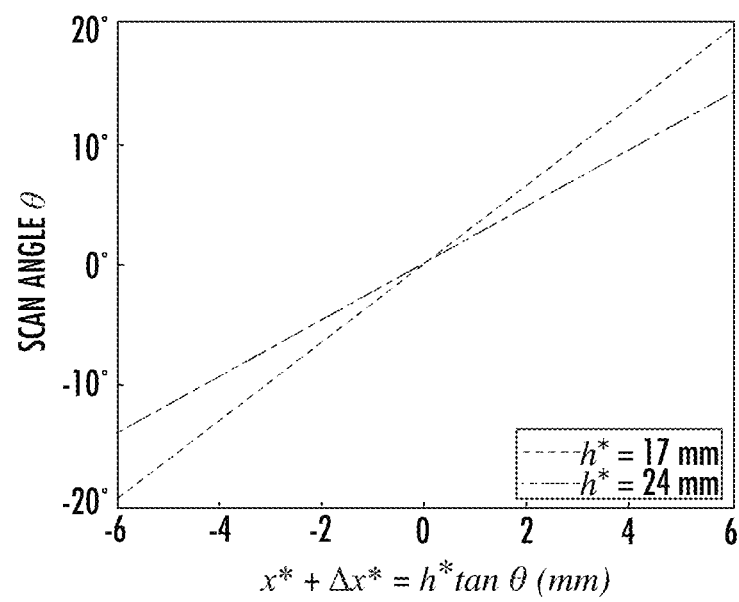
FIG. 12D is a graph illustrating the imputed scan angle for choosing a scanning arc length of h*=17 mm or h*=24 mm, covering equal distance x*+Δx*=h*tan θ on a tangential plane in accordance with some embodiments of the present inventive concept.

Another condition that leads to ambiguity is specifying the total axial length as the distance of interest, rather than posterior chamber length $\overline{NP}$. Axial length is easier to measure than posterior chamber length because of the superior reflectivity from the cornea compared to the posterior edge of the eye lens. Therefore, a method of calibration adopted is to calibrate a scan distance, measured on a flat surface, and attribute that to a scan angle using the axial length. The imputed scan angle for choosing a scanning arc length of h*=17 mm or h*=24 mm, covering equal distance x*+Δx*=h*tan θ on a tangential plane is shown in FIG. 12D. Thus, care must be taken to specify the method of calibration both for accuracy of measurements on a known artifact, as well as to recover accurate measures on specific subjects.

In some embodiments of the present inventive concept it is desired to specify a model eye as a calibration phantom with the following attributes: The model eye will have an anterior optic that mimics emmetropic behavior of a human eye that focus a collimated beam of optical radiation to a backplane that simulates a retina. As used herein, "emmetropic" refers to the normal refractive condition of the eye in which with accommodation relaxed parallel rays of light are all brought accurately to a focus upon the retina. In some embodiments, the model eye consists of a centered optical imaging system having a first converging optical element that simulates a cornea, an aperture stop of fixed or variable diameter D1 that simulates a pupil, a second converging optical element that simulates an eye lens, characterized by an optical axis, a backplane-side nodal point, a focal backplane, and a field of view 2θ. The backplane has a defined negative radius of curvature R centered on the optical axis and a clear aperture diameter D2. The distance from the nodal point to the pole of the backplane, along the optical axis, is a defined distance h. The field of view 2θ, where θ is the angle measured from the optical axis at the nodal point to an edge of the backplane at the radial limit of the clear aperture, is unobstructed by features of the housing that constrains the model eye. The model is encased in mechanical housing for mounting, aligning, and preserving the spacings of the elements in a closed fluid-fillable environment.

Figures 14A, 14B:
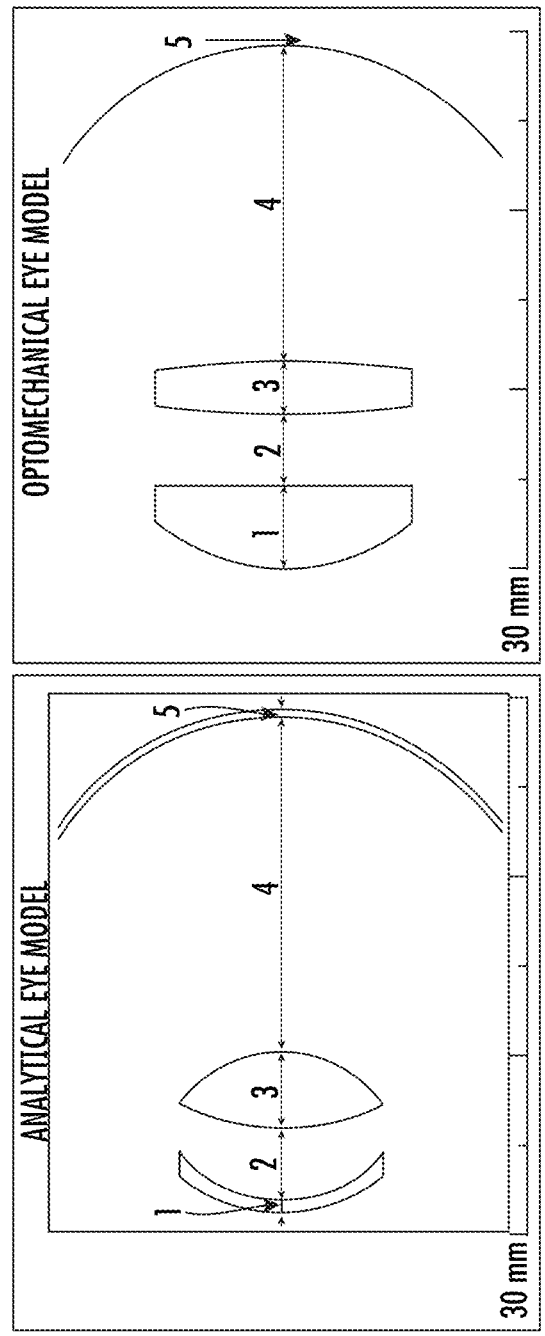
FIG. 14A is a diagram illustrating an analytical eye model in accordance with some embodiments of the present inventive concept.
FIG. 14B is a diagram illustrating an optomechanical eye model in accordance with some embodiments of the present inventive concept.

An Anatomical Model Eye (AME) of the present inventive concept is illustrated in FIGS. 14A and 14B. In particular, FIGS. 14A and 14B provide optical schematics of the analytical (14A) and the optomechanical (14B) eye models. All the elements of the eye including cornea (1), anterior chamber (2), crystalline lens (3), posterior chamber/vitreous cavity (4) and retina (5) are reported. Thus, as illustrated, the AME (FIG. 14A) has a spherical inner surface posterior to a focusing anterior objective lens assembly, a pupil plane corresponding to the nodal point of the focal assembly, a posterior distance from the pupil plane to the posterior pole of the spherical surface, and fiducials imprinted on the inner surface. In some embodiments of the inventive concept, the radius of curvature of the posterior surface is specified, and the radius of curvature is smaller than the posterior distance from pupil to posterior pole. The anterior focal assembly focus the image of an object at infinity in a Maxwellian fashion to the central region of the inner surface, for example, the posterior pole of the system. As such, the AME is a model of an emmetropic human eye. The posterior chamber length is designed at 17 mm. The radius of curvature of the inner "retina" surface is 13 mm. The refracting power of the anterior objective lens assembly is nominally 60 Diopters. Specific parameters of a model eye that satisfy this set of criteria are listed in the Table 1400 of FIG. 14C.

The model is based on a simplified version of the Dubbelman schematic eye derived from Scheimpflug biometric measurements of the human eye. In the simplified model, all refractive surfaces are spherical in shape. Surface curvatures, intraocular distances are set (Table 1400) to reproduce a relaxed adult eye (35 years, 0 D accommodation). The optical model is plotted in FIG. 14A. The eye model contains a 5 mm pupil and a curved retina with a radius of 13 mm. Refractive indices of the cornea and ocular media are taken from Gullstrand except for the lens for which a uniform "equivalent" refractive index is adopted instead of the gradient since the goal is to model paraxial behavior only. With an axial length of 24.35 mm, an effective focal length of 16.70 mm (refractive power ~60 D) and the object at infinity the eye is emmetropic for the paraxial rays.

In some embodiments of the AME, the posterior chamber may be fluid filled with, for example, a balanced saline solution to mimic the vitreous. The pupil plane may include an aperture of diameter between 3 mm and 7 mm, and this aperture may be controlled via a blade shutter mechanism or may be a replaceable component. The anterior lens assembly in a preferred embodiment is a replaceable element. The anterior lens assembly may be a single, uncorrected, 60 Diopter singlet, or may be designed as per Table 1400 of FIG. 14C to include a pair of lenses that mimic the cornea and the crystalline lens, respectively. The crystalline lens assembly may also be replaced with intraocular lenses of the type used in cataract replacement surgery.

In some embodiments of the present inventive concept, illustrated in FIGS. 14A through 14E, the model eye is constructed of the following: an anterior lens assembly comprising a plano convex singlet lens with a radius of curvature 10.3 mm and a thickness of 3.98 mm, and refractive index (at 550 nm) of 1.519 (Thorlabs LA1074), a double convex lens with front and back radii of curvature of +−30.36 mm and a central thickness of 2.59 mm. The two lenses are separated by 3.0 mm in a saline filled chamber (n=1.33), with a pupil deposed between the two lenses in substantial proximity to the double convex lens. A posterior backplane substrate is constructed of a spherical plano concave lens with a radius of curvature of −13.8 mm. (Thorlabs LC4253). It will be understood that these details are provided as example only and embodiments of the present inventive concept are not limited thereto.

In some embodiments of the present inventive concept, the pupil is centered on the optical axis with a diameter D1 between 3 mm and 7 mm.

The mechanical model, illustrated in FIG. 14B and tabulated in FIG. 14C, is a close optical replica of a physiological analytical model, FIG. 14A, using off the shelf optical components. The mechanical model focuses to a constant radius of curvature of 13.0 mm posterior to the double convex lens, shown in FIG. 13D. An off-the-shelf optic as the posterior substrate of −13.8 mm is selected for convenience, though a custom optic could be manufactured. FIG. 14E illustrates the correspondence between the external visual angle and the internal scan angle.

The substrate is centered on the optical axis and potted to a mechanical mount that forms the cap of the assembly. A chamber separating the posterior surface of the double convex lens and the pole of anterior surface of backplane substrate preserves the desired distance of 16 mm between lens and posterior pole for this design. 16 mm is the focal length of the anterior optical system from the rear lens surface, and −13 mm is the radius of curvatures of the focal plane.

In some embodiments, the SME is substantially equivalent to the AME, with the replacement of the retinal backplane having radius of curvature $|R|<h$ with a backplane matched to the chamber length, $|R|=h$.

Figure 15A:
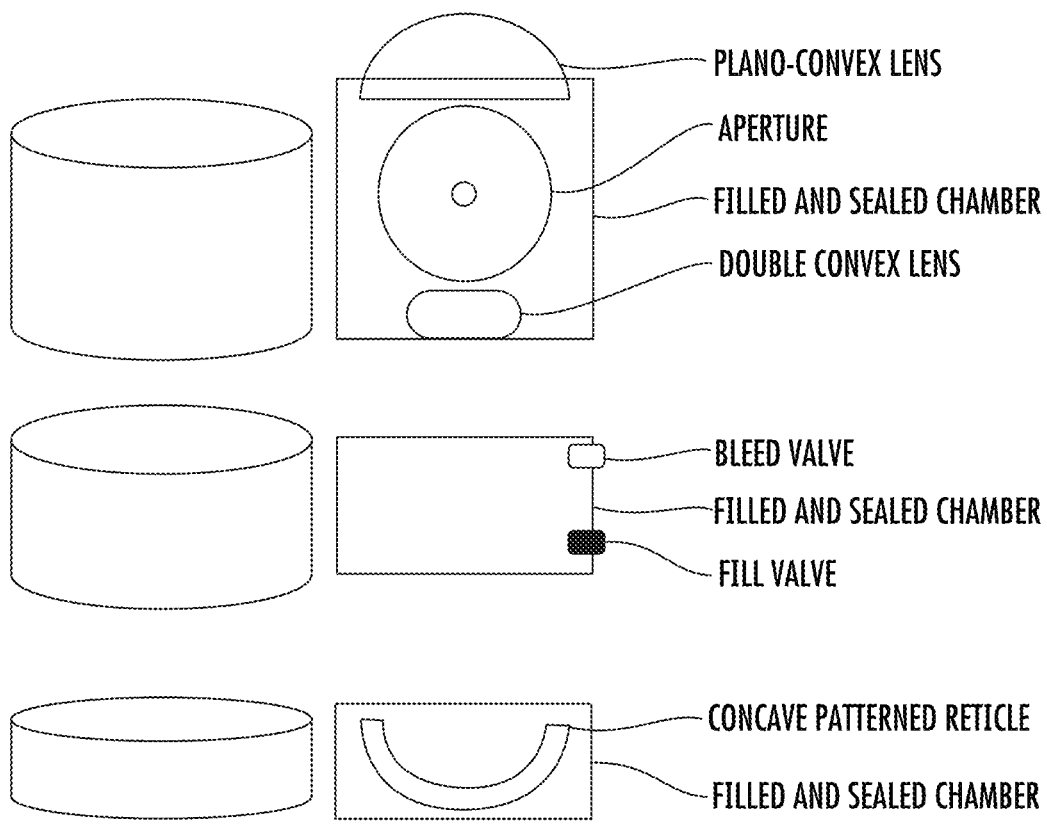
FIGS. 15A through 15C are diagrams illustrating a housing including three modules: the anterior module holding the lenses and pupil in a fluid-filled chamber; a posterior module, or cap, supporting the backplane, and a central module that preserves the distances in a fluid-filled chamber in accordance with some embodiments of the present inventive concept.
Figure 15B:
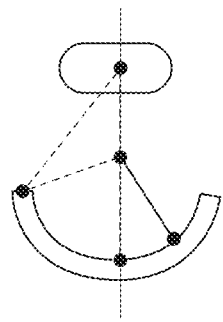
Figure 15C:
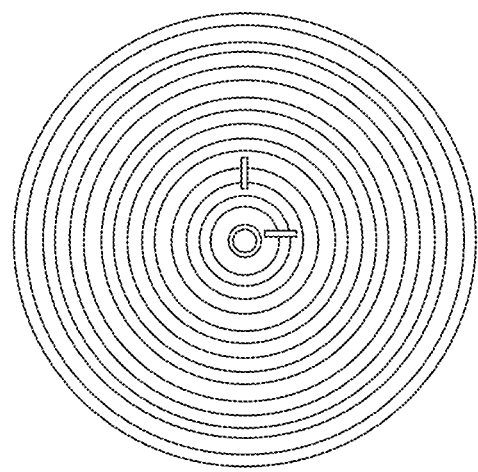

In these embodiments, schematically diagrammed in FIGS. 15A through 15C, the housing is composed of three modules: the anterior module holding the lenses and pupil in a fluid-filled chamber; a posterior module, or cap, supporting the backplane, and a central module that preserves the distances in a fluid-filled chamber. In some embodiments, the housing may be aluminum, milled from engineered polymers, or 3D-printed without departing from the scope of the present inventive concept. The posterior module and central module may be attached via opposing male-female threads. The anterior chamber and central chamber may also be connected by threads.

It is desirable to have a mechanism to fine tune the posterior chamber depth. Therefore the threading or the anterior to central modules allow control over a range of 3 to 5 mm about the target posterior chamber length, with a precision of about 0.1 micron. This is achievable with standard ISO threads, for example, an M30 (30 mm diameter) fine pitch thread (2.0 mm pitch) can provide an adjustment of 100 microns in an 18 degree twist, or ⅕ of a full revolution. This would be well suited to providing a range and precision of adjustment necessary to achieve and maintain a target geometry.

The anterior chamber in these embodiments is a fluid-filled, sealed unit, as is the posterior cap. Filling of the central chamber can be accomplished after assembly and spacing adjustment with a fill port, for example, using a valve accessed with a piston syringe and a bleed valve.

Figure 16A:
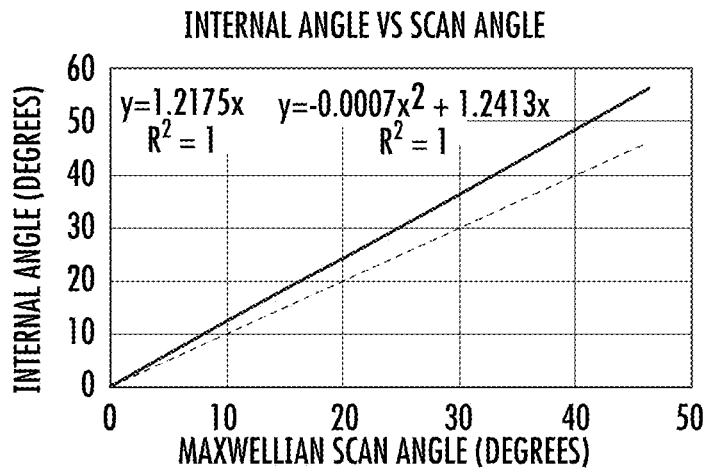
FIGS. 16A through 16C are graphs illustrating performance of model eye embodiments illustrated in FIGS. 15A through 15C in accordance with some embodiments of the present inventive concept.
Figure 16B:
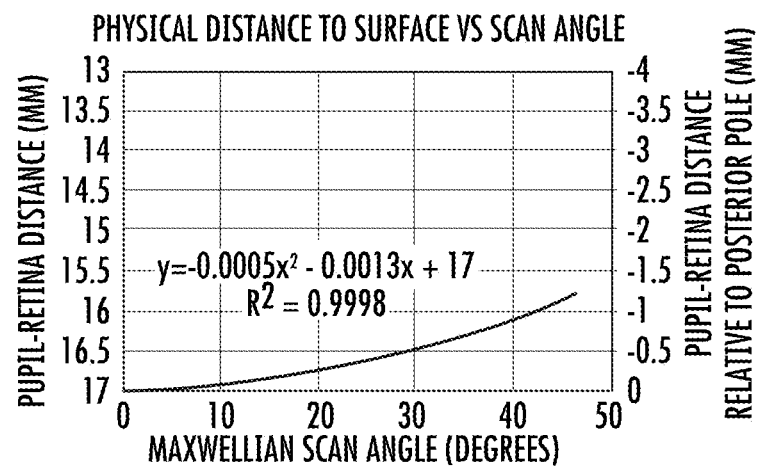
Figure 16C:
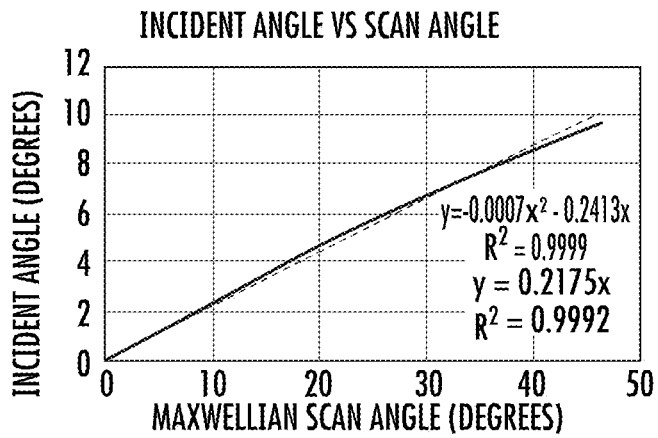
Figure 17A:
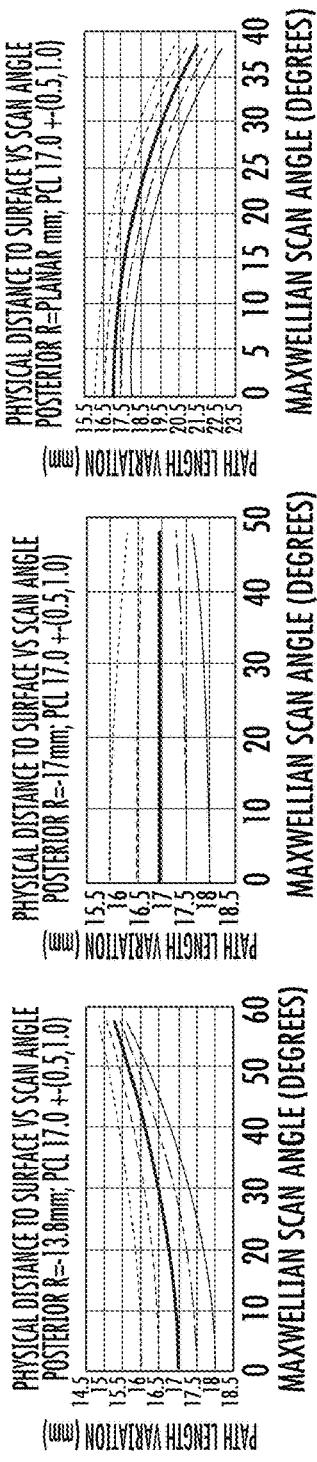
FIGS. 17A through 17F are graphs illustrating performance for the three classes of backplane in accordance with some embodiments of the present inventive concept.
Figure 17B:
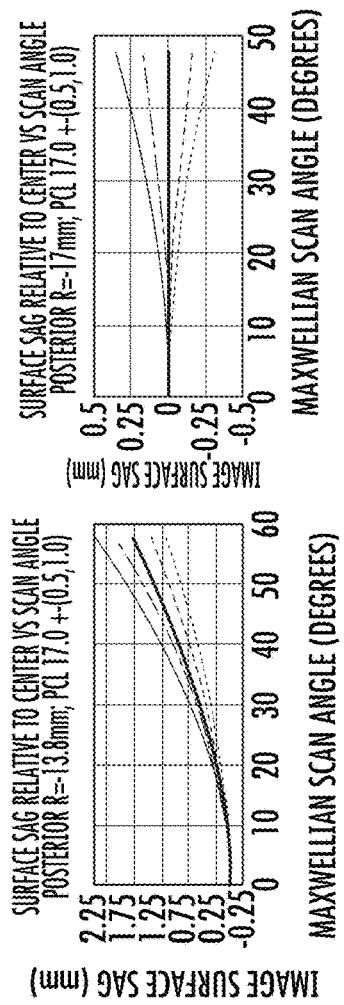
Figure 17C:
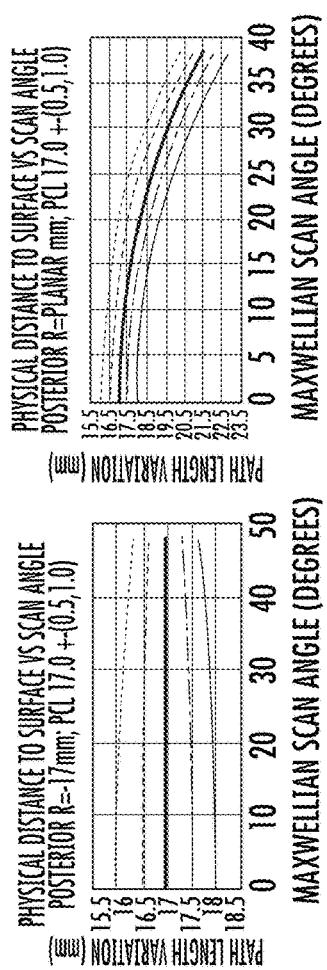
Figure 17D:
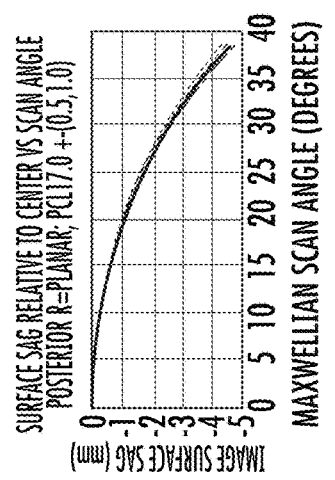
Figure 17E:
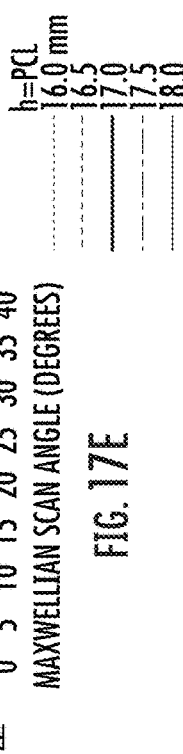
Figure 17F:
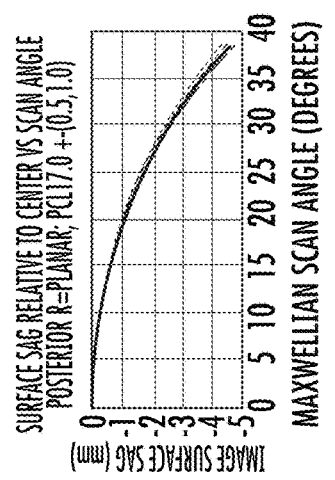

The performance of model eye with a backplane radius of curvature R=−13 mm and h=17 mm in accordance with some embodiments of the present inventive concept will now be discussed with respect to FIGS. 16A through 16C. This model provides a full 90 degree (2θ) FOV. FIG. 16A is a graph illustrating the central (or internal) angle versus the Maxwellian scan angle; the central angle is 22% larger than the Maxwellian angle in a linear relationship over this scan range. The expected surface sag is shown in the graph of FIG. 16B. The image will have an edge-center sag of approximately 1.25 mm due solely to scan geometry relative to the backplane center of curvature. Finally, as illustrated in FIG. 16C, the incident angle of a scanning ray with the backplane increases with scan angle (angle β from Eqn. 9). Dependent on the refractive index difference between the posterior chamber fluid and the substrate (or features overlaying the substrate), this angle of incidence can be a cause of refraction that distorts underlying features or measurements. This effect is small for the vitreous-retina interface, ($n_{vitreous} \cong 1.33$, $n_{retina} \cong 1.36$) but is non-zero at increasing angles of incidence.

These embodiments perform close to an emmetropic (normal) adult eye. As alluded to in earlier calculations, the pediatric eye is significantly smaller, with a smaller radius of retinal curvature. The same design concepts may be applied to model the pediatric eye, or any other specific eye geometry that is desirable.

In some embodiments of the present inventive concept, a substrate with a radius of curvature that matches the nodal distance is proposed; this is the SME. In these embodiments, the anterior optics of embodiments discussed above are maintained, and the posterior backplane is replaced with a spherical concave lens with a radius of curvature of −17 mm (e.g. −37 Diopter fused silica plano-concave lens). For this radius of curvature, the scan height is constant across the FOV. Adjusting the posterior chamber depth using the threaded assembly while imaging on a reference imaging device until the image surface is flat will increase the likelihood or possibly ensure that the geometry is precise. The extent to which the surface cannot be flattened, for example, residual of a linear fit to the surface, is a direct measure of non-sphericality of the surface of constant OPLD of the model eye.

In some embodiments of the present inventive concept, the posterior substrate may be flat. In this case R=−∞, and the calculations may still be completed. However, the scan distance to sample increases rapidly with angle present two significant problems. First, the sample will be increasingly out of focus as the scan range increases. Second, an OCT image has a limited range of depth for imaging, and the image will curve out of the FOV rapidly. Therefore while a flat surface can be used, the range of applicability is quite limited.

FIGS. 17A through 17F are graphs illustrating performance for the three classes of backplane: the backplane that most closely resembles the human retina with a radius of curvature R=−13.8 mm smaller than the nodal, or posterior chamber, length; the backplane with a radius of curvature R=−17 mm that matches the nodal distance, with the objective of imaging the surface to a flat line of constant OPLD; and the flat backplane R=∞ (planar), which presents the surface as a highly outwardly curved image (sharply increasing OPLD as a function of scan angle) with a limited FOV.

In some embodiments of the present inventive concept, a pattern is etched, engraved, deposited, or otherwise applied to the backplane. The pattern may be either hyper- or hypo-reflective, so long as the pattern is visible with the imaging system under calibration.

In some embodiments of the present inventive concept, the pattern is a chrome-on-glass pattern deposited onto the surface of the backplane. The chrome-on-glass pattern provides a hyper-reflective surface to the imaging system In some embodiments of the inventive concept, the pattern is etched into a conformable lithographic photomask that is directly applied to the surface, such that the differential reflectivity between the mask and the backplane substrate provides a viewable pattern for the imaging system In some embodiments of the present inventive concept, the applied pattern has a rotational symmetry and a radial repeat unit. In some embodiments, the pattern consists of series of concentric annular rings, each ring having a diameter and a width, with the diameter of each successive ring being sufficiently larger that there is space between the rings. In some embodiments of the inventive concept, the pattern of rings substantially fills the clear aperture of the substrate.

In some embodiments of the present inventive concept, the width w of each ring is the same, $w_i=w$, and the spacing between successive rings is equal to the width of the ring. This pattern may be considered to a duty cycle of 0.5 and the diameter $D_n$ of the nth ring is equal to $D_{n+1}=D_n+2w$.

In some embodiments of the present inventive concept, the width w of each ring is the same, $w_i=w$, and the spacing between successive rings is equal to an integer multiple m of the width of the ring. This pattern may be considered to have a duty cycle of $1/(m+1)$ and the diameter $D_n$ of the nth ring is equal to $D_{n+1}=D_n+2(m)w$.

In some embodiments of the present inventive concept, a pattern is applied to each of the available backplanes. The pattern is a series of concentric rings of constant width and increasing diameter extending substantially across the clear aperture of the substrate. In some embodiments the rings are chrome-on-glass deposited through a conformable photolithography mask, centered and pressed to the surface of the substrate. The first ring has an inner diameter of 160 microns and an outer diameter of 240 microns. The second ring has an inner diameter of 560 microns and an outer diameter of 640 microns. The third ring as an inner diameter of 960 microns and an outer diameter of 1040 microns, and so on, until 60 rings fill a 24 mm diameter of the substrate with a duty cycle, or fill factor, of 0.2.

Figure 31A:
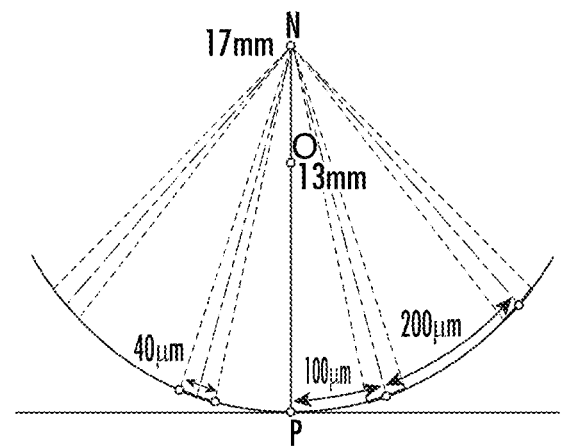
FIGS. 31A through 31C are diagrams of the application of the pattern in accordance with some embodiments onto three backplanes will be discussed.
Figure 31B:
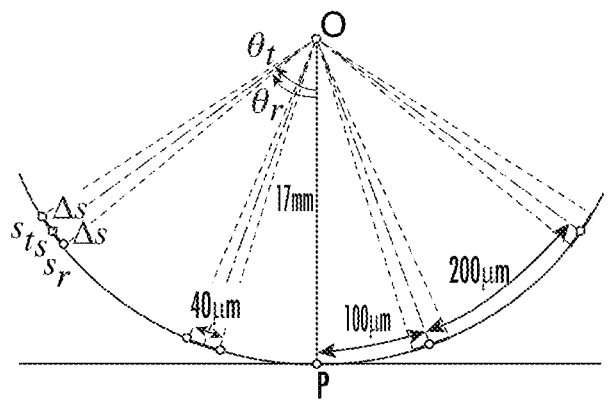
Figure 31C:
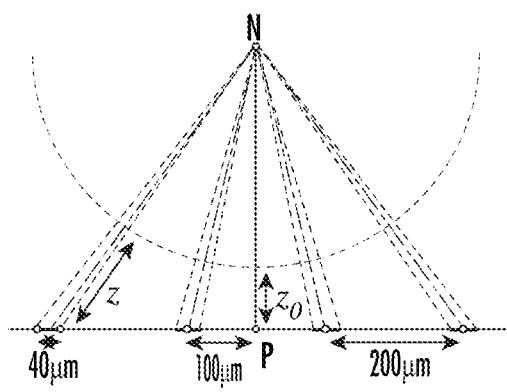

In FIGS. 31A through 31C, diagrams of the application of the pattern in accordance with some embodiments onto three backplanes will be discussed. In particular, in FIG. 31A: h=$\overline{NP}$=17 mm; R=$\overline{OP}$=−13 mm. This is an illustration of a vertical slice of a calibration phantom with a posterior chamber length greater than the radius of curvature of the posterior surface (nodal point not at the center of curvature). It will be understood that the scan angle is no longer equal to the central angle, so the arc length is no longer proportional to the scan angle. In FIG. 31B: h=R=17 mm. This is an illustration of the positions of the fiducial markings in a vertical slice of the calibration phantom with nodal point N at center of curvature (that is, the scan angle equals the central angle). The fiducial markings conform to the spherical surface, so the thickness (40 microns) of each ring and the distance between consecutive rings (200 microns) both correspond to arc lengths s measured along the surface from the pole P. In FIG. 31C: h=17 mm, R=∞ (planar). This is an illustration of the positions of the fiducial markings on a vertical slice of the flat substrate backplane with nodal point N. In an OCT image, the distance to the surface from the top of the B-scan would correspond to the distance z from the reference circle to the flat substrate.

Figure 18A:
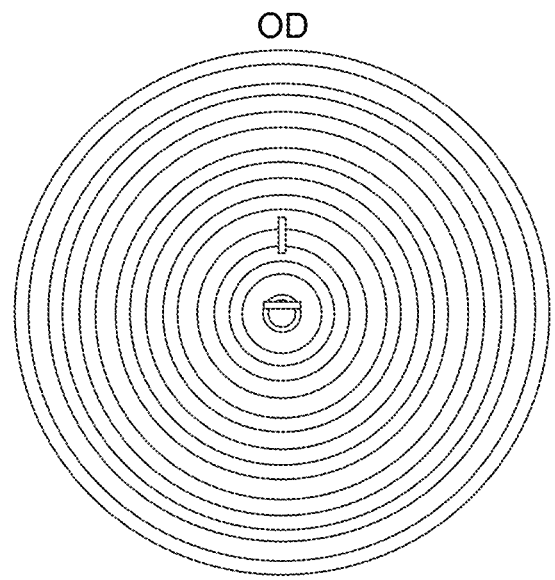
FIGS. 18A and 18B are diagram illustrating a right eye (OD) and left eye (OS) orientations in accordance with some embodiments of the present inventive concept.
Figure 18B:
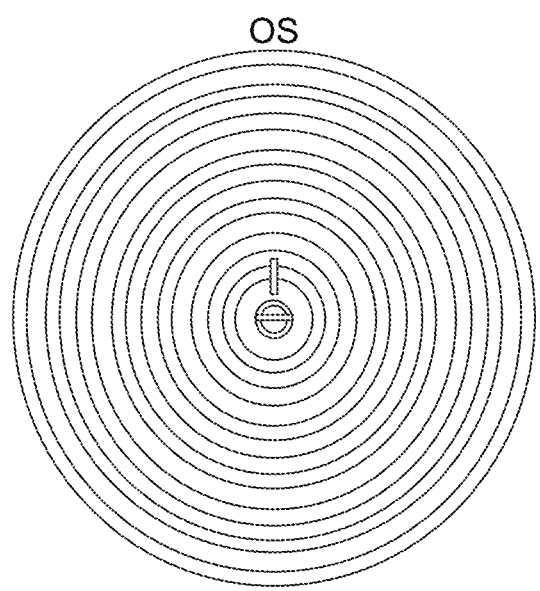

In some embodiments of the present inventive concept, a minimal indication of orientation of the substrate is provided with respect to rotation around the optical axis. Two small stripes are applied, a first stripe crossing a first ring and a second stripe crossing a different neighboring ring, as diagrammed in FIG. 15C. Nominally, the stripes are the width of the ring, and extend from the ring one width radially to and from the center of the substrate. The stripes are applied at 90 degrees from each other, pointing North and East respectively, in a first orientation. Such an orientation may be used to signify, for example, a right eye (OD). Rotating the model eye 90 degrees counter-clockwise moves the North indication to the West, and the East to the North. This orientation may be used to signify the left eye (OS). With these orientations, a tick mark pointing North is indicative of the Superior direction and pointing East in a right eye is a Nasal direction. Conversely, for the left eye, West is the Nasal direction. These orientations are shown in, for example, FIGS. 18A and 18B. These indicators are sufficient to eliminate any ambiguity in in the structural orientation and can ensure that any image inversion is properly interpreted.

In some embodiments of the present inventive concept, additional fiducial indicators of rotation, such as longitudinal radially extending lines may be patterned to provide additional guidelines for rotational calibration.

In further embodiments of the inventive concept, a set of fiducials is applied that is designed to calibrate lateral resolution as a function of position relative to the posterior pole of the SME. Uniquely, this resolution "phantom" is designed to provide information of multiple scales, using a fractal-like assembly of circles, as shown, for example, in FIG. 19. This is the simplest representation of a hexlet, having the desirable properties that the circles (in this embodiment six equal-radius circles surrounding a seventh same-radius circle) are all "kissing." These "kissing" circles are enclosed in an outer circle, itself tangent to, or "kissing" the six outer circles, and thus the pattern may be scaled at will to a similar construct of six circles around one, each of a radius three-times the previous radius. The radii in the embodiment illustrated in FIG. 19 scale to the power of three with each layer (r=1, 3, 9, 27, 81 . . . for layer 0, 1, 2, 3, 4 . . . respectively). As designed, this figure is printed at the pole, in locations centered at equal-angular separations radially from the pole in increments at least greater than the angular diameter of the pattern, and generally between 2 and 5 degrees, and rotationally at least along the major compass axes a 0, 90, 180 and 279 degrees, and additionally at the 45 degree lines as well. In some embodiments, the placements along the intermediate 45 degree lines may be offset by half a separation period for a greater positional coverage.

In some embodiments of the inventive concept, a printed circle of smallest radius is given a radius of 1.0 micrometer, comparable to the radius of a cone photoreceptor. The pattern is reproduced in three circumscribing layers (layers 0, 1, 2, and 3), with a maximum radius of the outer circumscribed circle of $1*3^3=27$ micrometers.

In more general embodiments of the inventive concept, the smallest printed unit circle has a radius between 0.5 micrometer (diameter of 1.0 µm) and 5 micrometers (diameter of 10 µm) and is arranged with between two and five layers around the primary unit.

Figure 20C:
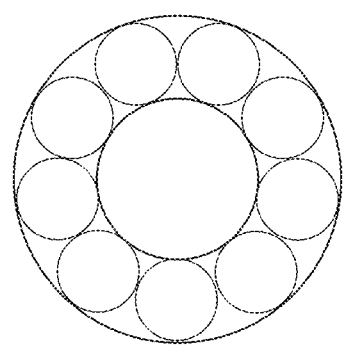
FIGS. 20A through 20C are diagrams illustrating Steiner Chains in accordance with some embodiments of the present inventive concept.
Figure 20B:
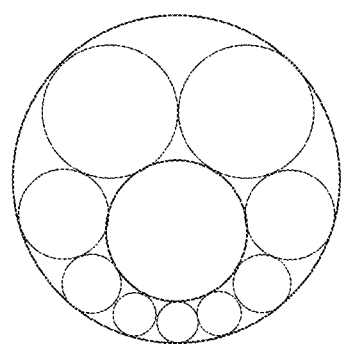
Figure 20A:
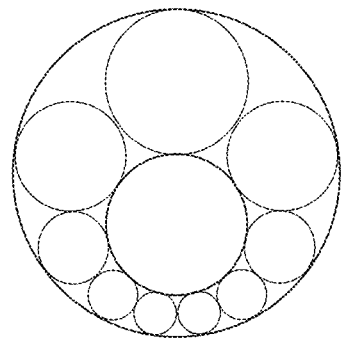
Figure 21A:
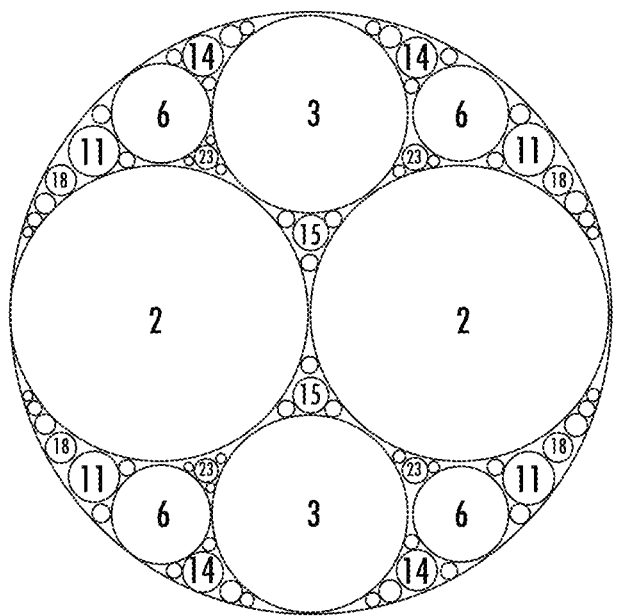
FIGS. 21A and 21B are diagrams illustrating Apollonian Circle Packings in accordance with some embodiments of the present inventive concept.
Figure 21B:
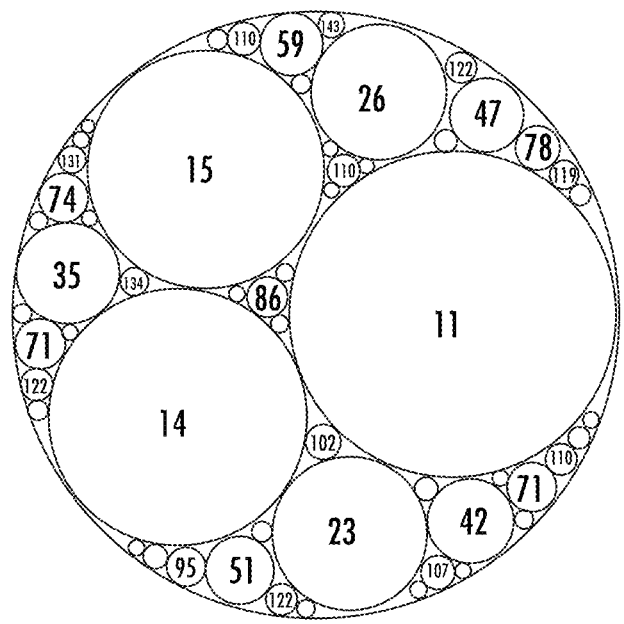

In further embodiments, any hexlet construction may be defined that meet the criteria of "kissing," and the design concept may further be extended to Steiner Chains illustrated, for example, in FIGS. 20A through 20C and Apollonian Circle Packings illustrated in FIGS. 21A and 21B. FIG. 21A illustrates an Apollonian Circle packing (−1, 2, 2, 3) and FIG. 21B illustrates an Apollonian Circle packing (−6, 11, 14, 15). FIGS. 20A through 20C and FIGS. 21A and 21B illustrate embodiments that meet the conditions of a tangential packing of circles within a circle, such that the packing may be expanded concentrically to provide a test plate at multiple scales.

A difference between the simplest hexlet of FIG. 19 and the those illustrated in FIGS. 20A through 21B, is that the diameters of the simple hexlet of FIG. 19 scale as integer powers of 3, whereas in the other patterns there is a greater variety of diameters for a more finely resolved imaging scale. It will be understood that FIGS. 19 through 21B are provided as examples only and that other such geometries may be also used without deviating from the intent of the inventive concept.

Figure 22:
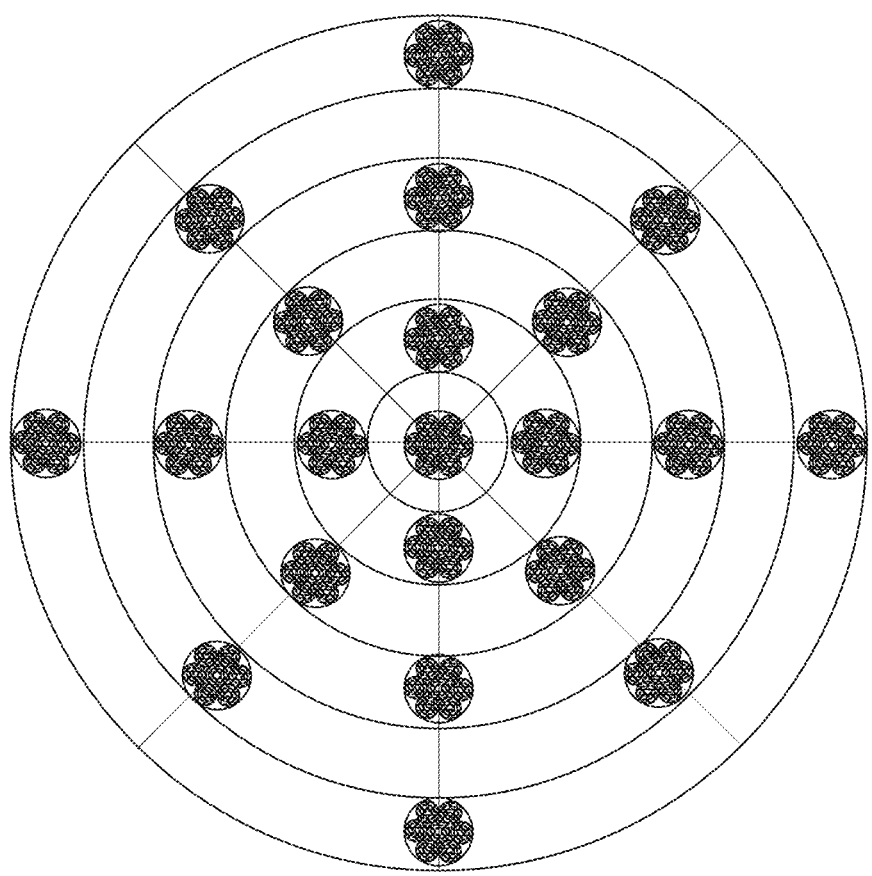
FIG. 22 is a diagram illustrating a representative patterning of rings and hexlets on the backplane of a calibration phantom in accordance with some embodiments of the present inventive concept.

In some embodiments of the present inventive concept, the spherical eye model (SEM) may include a spherical inner surface, cartographic fiducials mapping out orthogonal angular spacings in spherical coordinates, a translucent layered structure of dimension of the order of major retinal layers, and a multi-scale resolution test pattern placed strategically at the posterior pole of the SME, at increasing eccentricities away from the pole towards the scanning periphery at rotational positions around the pole at various eccentricities, as illustrated, for example, in FIG. 22.

In some embodiments, precision in the posterior surface curvature and the posterior chamber length are maintained to support accurate calibration. The spherical posterior surface may be produced using grinding, polishing, diamond turning, casting, or molding technologies. The optimum target surface flatness expressed as a deviation from spherical target is equal to the axial resolution of the imaging system, i.e., between 3 and 10 micrometers. The spherical surface preferable extends to 30 degrees or more beyond the pole enabling calibration of widefield scanning systems.

In some embodiment of the present inventive concept, the patterned substrate is overlayed with a sequence of layers that mimic light transmission and reflection from the retina. In contrast to the Rowe device (OEMI-7) discussed above, the goal is not to provide features that demonstrate physiological or pathological structures, rather to provide a quantifiable and reproducible set of structures to measure thicknesses as a function of image angle, and to measure signal to noise as a function of depth in OCT images. In some embodiments of the present inventive concept, the total attenuation through such a layered stack is limited to 6 dB or 3 dB, well within the dynamic range of an OCT system, and insufficient to hide the chrome-on-glass features applied under the layers.

Figures 23A, 23B:
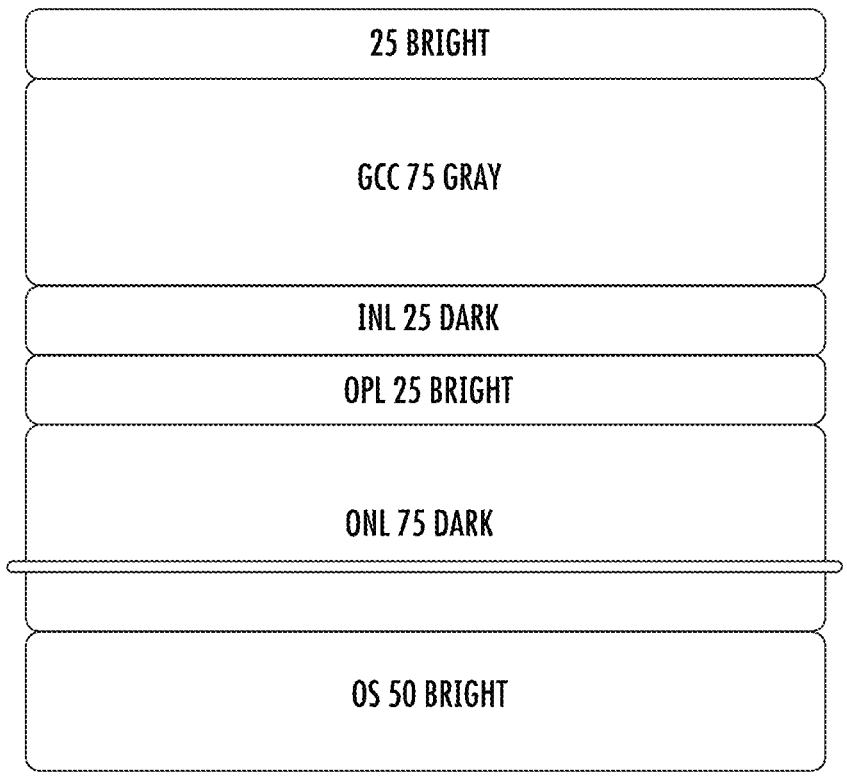
FIG. 23A is a diagram illustrating a representative layer stacking on the backplane of a calibration phantom with an alternating sequences of layer thickness and perceived reflectivity that loosely align to retinal structures in accordance with some embodiments of the present inventive concept.
FIG. 23B is a table detailing layer thickness relative attenuation coefficients, attenuation coefficients (dB/um) and total layer attenuations in accordance with some embodiments of the present inventive concept.

FIG. 23A illustrates a specific layer stack with an alternating sequences of layer thickness and perceived reflectivity that loosely align to retinal structures. Layer thickness relative attenuation coefficients, attenuation coefficients (dB/um) and total layer attenuations are tabulated in the Table 2300 of FIG. 23B. In some embodiments, these structures may be constructed with 3D printing. This will work fine on flat substrates, and the materials can be pre-engineered with available printable polymers combined with additives to achieve the desired optical properties. For the curved substrates, the 3D printing may be suboptimal, due to the print resolution and the way the printed material forms when transitioning from melt to solid phase. The layers, with current printing technologies, will be stair-cased and irregular. Instead, translucent polyethylene, polyester, and vinyl substrates with silicone, rubber, or acrylic adhesives can be engineered to achieve target thicknesses and optical properties and applied as single sheets to the substrate to build even layers across the FOV. Custom engineering of such layers may not be practical from a cost perspective. An alternative is to build a close proximity of the target layered structures from commercially available industrial bi-layer (substrate plus adhesive) tapes, such as from 3M. Examples of available tapes include, for example, 3M 335 with a polyester base and rubber adhesive; 3M 850 with a polyester base and acrylic adhesive; 3M 860 with a thick polyester base and adhesive blend; 3M 5151 with a PFTE base embedded with glass and a silicone adhesive; 3M 5480 with a PFTE base only and a silicone adhesive; 3M 840x and 890x with Polyester base and silicone adhesives; and the like.

Figures 32A, 32B:
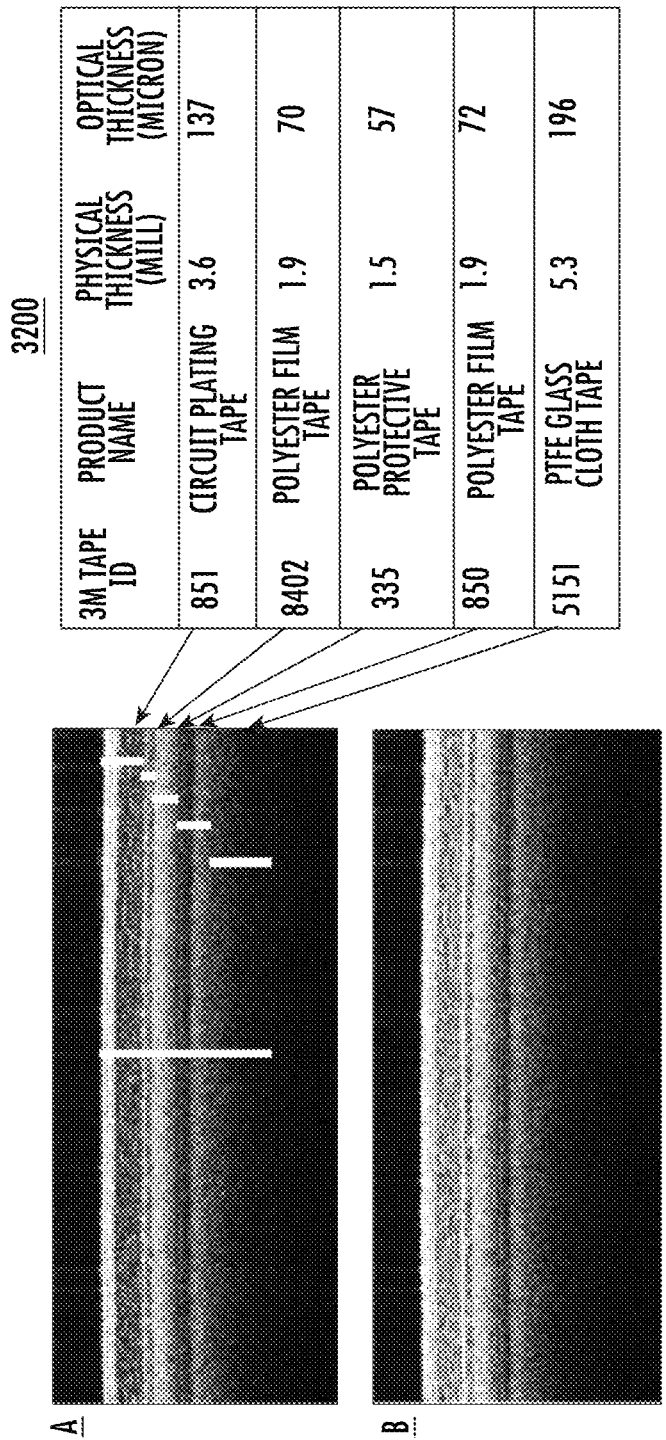
FIG. 32A illustrates Bscans (A and B) of the same sample at different optical polarization settings in accordance with some embodiments of the present inventive concept.
FIG. 32B is a table 3200 including an ordered list of the adhesive tapes, with specified thickness in mills (0.001 inch), and estimated optical thickness in microns, assume a refractive index of 1.5.

FIGS. 32A and 32B illustrate an OCT Bscan images (A and B) of one layer stack of 3M adhesive tapes according to some embodiments of the present inventive concept. As illustrated in FIG. 32B, the tapes are, from top to bottom: 3M 851 Circuit Plating Tape; 3M 8402 Polyester Film Tape; 3M 335 Polyester Protective Tape; 3M 850 Polyester Film Tape; and 3M 5151 PTFE Glass Cloth Tape. Bscans A and B of FIG. 32A are images of the same sample at different optical polarization settings, demonstrating further utility in polarization sensitive imaging. The table in FIG. 32B is an ordered list of the adhesive tapes, with specified thickness in mills (0.001 inch), and estimated optical thickness in microns, assume a refractive index of 1.5.

In some embodiments of the present inventive concept, the individual layers will range in thickness from 20 µm to 200 µm, with total stack thickness from a single 20 µm layer to a multi-stack of 300 µm to 600 µm, and preferably less than 1.0 mm in total thickness. In a further embodiment, at least one layer is between 2 µm and 5 µm in thickness.

In some embodiments of the present inventive concept, glass or polymer microbeads are dispersed between one our more layer pairs. The microbeads may be translucent or transparent, and may range in diameter from approximately 2 µm to approximately 20 µm. In a further embodiment, a first layer incorporates microbeads of a diameter and a second layer will incorporate microbeads of a second diameter.

It will be understood that specific parameters of the above embodiments provide representative examples of an appropriate model eye for quantitative calibration of Maxwellian view optical imaging systems. The specific requirement is to construct a model eye with well specified parameters discussed herein such that attributes of an image can be tested against the computational model, a correct scan angle versus applied signal may be derived, and a correct scan scaling can be applied to an image given a subject eye with a different set of parameters, and specifically posterior chamber.

In some embodiments of the present inventive concept, the model eye has a pupil diameter D1 sized in relation to the clear aperture D2 of the substrate such that D2/D1>2.

In some embodiments of the present inventive concept the ratio of backplane radius of curvature R is specified in proportion to the nodal distance h such that |R/h|>0.5.

In some embodiments of the present inventive concept the ratio of backplane radius of curvature R is specified in proportion to the nodal distance h such that 2.0>|R/h|>0.5.

In some embodiments of the present inventive concept the ratio of backplane radius of curvature R is specified in proportion to the nodal distance h such that 7/5>|R/h|>2/3.

In some embodiments of the present inventive concept the ratio of backplane radius of curvature R is specified in proportion to the nodal distance h such that 1.10>|R/h|>0.90.

In some embodiments of the present inventive concept the ratio of backplane radius of curvature R is specified in proportion to the nodal distance h such that 1.05>|R/h|>0.95.

In some embodiments of the present inventive concept the useable field of view 2θ>40 degrees.

In some embodiments of the present inventive concept the useable field of view 2θ>60 degrees.

In some embodiments of the present inventive concept the useable field of view 2θ>80 degrees.

In some embodiments of the present inventive concept the useable field of view 2θ>100 degrees.

The following methods may be used in calibrating Maxwellian-view imaging systems using the described phantom, or model eye. As discussed above, the lateral width of the OCT window is the arc length of the circle swept by the scan, and therefore the lateral dimension, or width $w_{scan}^{top} = (2\theta)*(\pi/180)*h^{top}$ and $w_{scan}^{bottom} = (2\theta)*(\pi/180)*h^{bottom}$ which are not the same. For an adult eye of h=17 mm and an OCT window depth $z_{max}$=3 mm, $w_{scan}^{top} \cong (0.84)*w_{scan}^{bottom}$.

In an original calibration of an imaging system, the anatomical model eye with nodal distance h and radius of curvature R is aligned at the appropriate working distance for the imaging system. The scan range is set at the imaging system according to the specific controls of the imaging system, for example, a linear scan range or an angular scan range. An image is acquired. The pattern with known spacing is analyzed, and the known spacing are mapped to the system known controls to create a calibration function. In some embodiments, the function is preserved in a form $\theta = f(S_{device}; h_{phantom}, R_{phantom})$ where $S_{system}$ is the device-specific control signal, $h_{phantom}, R_{phantom}$ preserves the record of the calibration phantom, and the system preserves the angular calibration referenced to the Maxwellian-angle θ. Images may then be recorded and displayed as a function of angle.

When imaging a subject, for example, a human patient, with a known posterior chamber length, the lateral scan width can be correctly calculated as follows:

$$\langle y_{max} \rangle = (\theta_{max})*(\pi/180)*\langle h \rangle \qquad \text{Eqn. (25)}$$

where the $\langle \ \rangle$ is meant to indicate that the value reflects the scan width at the location of the depth in the OCT image of the retina at scan center. This illustrates that lateral spacing is in fact linear with scan angle, as opposed to the commonly applied tangent approach, and varies slightly, but not trivially, from the top to the bottom of the image window. Adopting this approach requires incorporating a measure of ocular biometry, for example obtaining a measurement with a Zeiss IOLMaster or a Haag-Streit Lenstar biometry device, and will lead to significantly improved interoperability among imaging systems, and greater accuracy for precision quantification of retinal images.

Figure 24A:
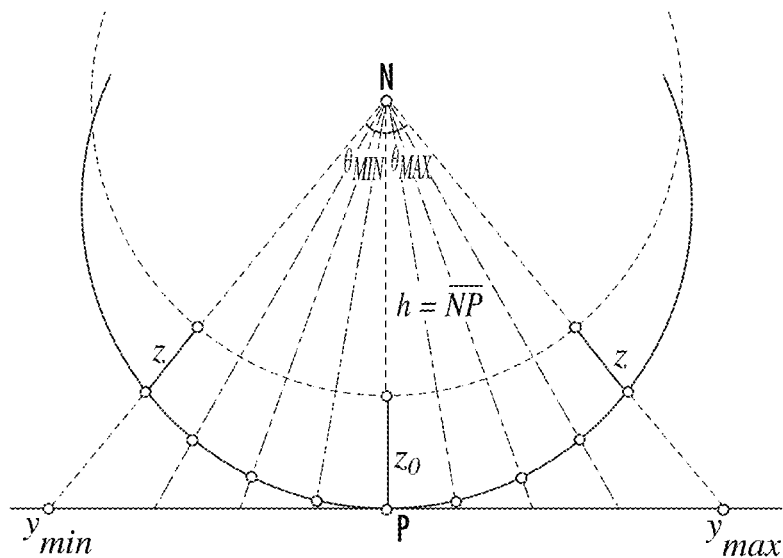
FIGS. 24A and 24B are graphs illustrating the scan angle θ obtained from the imaging data by imaging the inventive model eye patterned fiducial markings that are positioned on the surface either at equal angular spacing (FIG. 23A) or according to an angle θ between the nodal point and the optical axis so that the values h tan θ are equally spaced (FIG. 24B) in accordance with some embodiments of the present inventive concept.
Figure 24B:
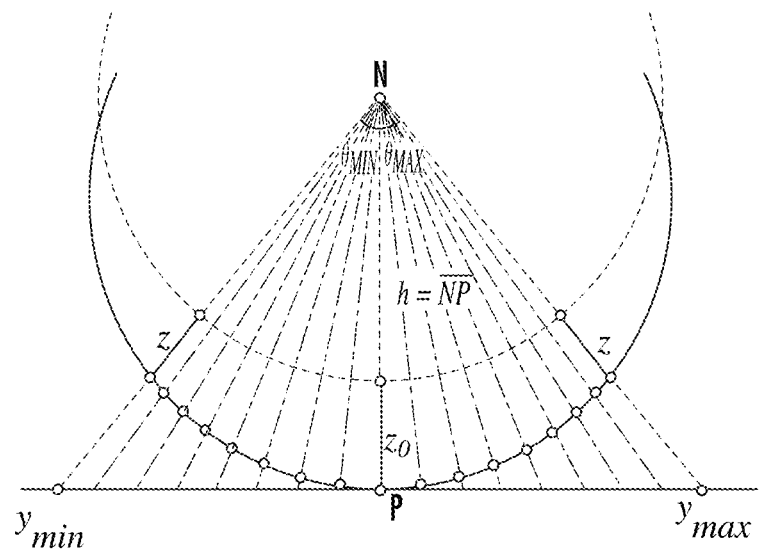

Re-Calibrating an imaging device using the patterned fiducials in accordance with some embodiments of the present inventive concept will now be discussed. For simplicity, assume the OCT scanner is initially calibrated according to ISO 16971 and uses $y^* = x^* + \Delta x^*$ along with the user-specified scan range $[y^*_{min}, y^*_{max}]$, where $y^*_{min} = -y^*_{max}$, and determines the scan angle θ using an assumed value $h^*$ based on the relationship $y^* = h^* \tan \theta$ (where $h^*$=17 from ISO 16971). A-scans are sampled at some periodicity defined by the system controller across the scan range. As the system controls scan angle and sweeps the angle via an applied signal (e.g. voltage) as a function of time, the most direct sampling is that A-scans are sampled at constant angular increment $\Delta\theta = \theta_{max}/(N-1)$ where N is the number of A-scans in a sweep (e.g. in a B-scan). We note that this sampling interval need not be assumed and need not be linear. The scan angle θ directly can be obtained from the imaging data by imaging the inventive model eye patterned fiducial markings that are positioned on the surface either at equal angular spacing (FIG. 24A) or according to an angle θ between the nodal point and the optical axis so that the values h tan θ are equally spaced (FIG. 24B). Thus, the OCT device's value of $h^*$ can be computed from the value $y^*_{max}$ that is set by the user. That is, $$h^* = \frac{y^*_{max}}{\tan(\theta_{max})} = \frac{y^*_{min}}{\tan(\theta_{min})}.$$

Furthermore, we can use the values θ and $y = x + \Delta x = h \tan \theta$ at each of the fiducial markings to determine whether the A-scans are spaced according to x or according to θ.

Figure 25A:
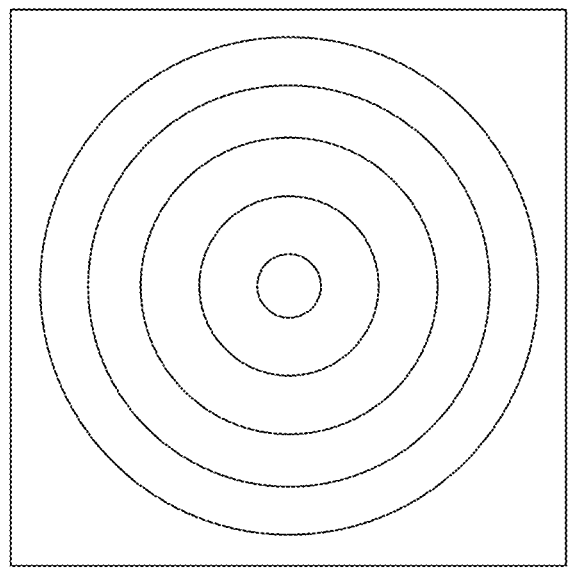
FIG. 25A is a diagram illustrating the projections of the fiducial markings onto a horizontal plane in accordance with some embodiments of the present inventive concept.
Figure 25B:
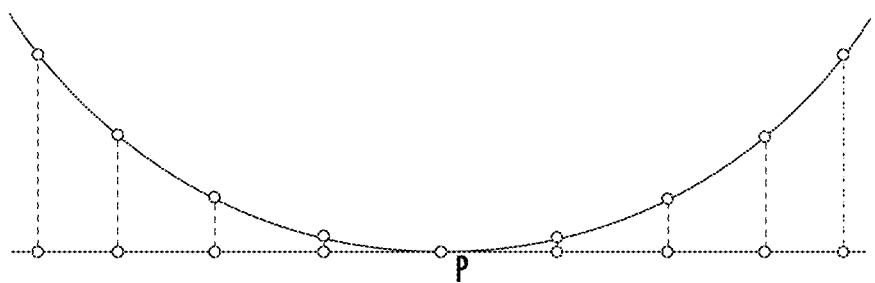
FIG. 25B is a diagram illustrating the projections of a pattern applied to a substrate of radius $|R|<\infty$ in accordance with some embodiments of the present inventive concept.

FIG. 25A shows the projections of the fiducial markings onto a horizontal plane, for example, as would be observed in an uncorrected enface projection or C-slice. FIG. 25A is a direct representation of a planar (R=∞) pattern, or the project of a pattern applied to a substrate of radius |R|<∞ as shown in FIG. 25B. Notice that the distance x can be determined from each projected ring to the optical axis in terms of the known values R and h of the calibration phantom using the formula discussed above in Case III:

$$x = R \sin \theta \sqrt{1 - \left(\frac{h-R}{R} \sin \theta\right)^2} + (h-R) \sin \theta \cos \theta \quad \text{Eqn. (26)}$$

Lastly, due to imperfections in the internal optics, each OCT system has a certain amount of intrinsic error in the depth measurement $\hat{z}$ that is a function of both the scan angle and the rotational orientation of the B-scan, i.e., error in the "flatness" of the scanning field. If it is assumed that there is no error in the scanning field flatness at the pole, the measured value $\hat{z}_0$ and the now-known scan angle $\theta$ can be used to compute the predicted value of z at each point; that is, the value we would expect to measure without any field flatness errors due to the scanner's optics:

$$z = \hat{z}_0 + R\left(\sqrt{1 - \left(\frac{h-R}{R} \sin \theta\right)^2} - \cos \theta\right) - h(1 - \cos \theta) \quad \text{Eqn. (27)}$$

The difference between this value and the measured value for the corresponding A-scan produces the error for that specific scan angle in that specific B-scan. Note that z is being used here to be consistent with current data reporting conventions; however, note that the z-coordinate corresponds to the radial coordinate r in spherical coordinates. Since we use $\theta \in (-\pi/2, \pi/2)$ to refer to the scan angle (the polar axis), we will use $\phi \in [0, \pi)$ to represent the azimuthal axis, or the direction of the B-scan.

Once a sufficient number of points covering the entire surface have been approved, the scanning field flatness error $OPLD(\theta, \phi) = \hat{z} - z$ can be modeled using an order n finite polynomial expansion:

$$OPLD(\theta, \phi) = \Sigma_{i=0}^n c_i Y_i(\theta, \phi), \quad \text{Eqn. (28)}$$

where the polynomials $Y_i$ form an appropriate basis for $\mathbb{R}^3$. The specific set of orthogonal polynomials and the order n will depend on the behavior of the error, and the coefficients $c_i$ would be determined using the imaging data from the calibration phantom. If $W = [\hat{z}_0 - z_0, \ldots, \hat{z}_p - z_p]^T$ are the p data points corresponding to the directions $(\theta_i, \phi_i)$ where $\theta$ has been determined using the fiducial markings on the calibration phantom, then the coefficients $C = [c_0, \ldots, c_n]^T$ can be determined in matrix form by solving:

$$W = \Sigma C, \quad \text{Eqn. (29)}$$

where the matrix $\Sigma$ is given by:

$$\Sigma = \begin{pmatrix} Y_0(\theta_0, \phi_0) & \cdots & Y_n(\theta_0, \phi_0) \\ \vdots & \ddots & \vdots \\ Y_0(\theta_p, \phi_p) & \cdots & Y_n(\theta_p, \phi_p) \end{pmatrix}. \quad \text{Eqn. (30)}$$

Once C is known, the error function $OPLD(\theta, \phi)$ can be interpolated at any point in the data set and the corrected z measurements as $\hat{z}_i - OPLD(\theta_i, \phi_i)$ can be computed.

The scan can be further analyzed by direct analysis of the edges of each patterned ring. The following formulas provide the intermediary, left, and right edges of each ring in terms of arc length from the pole $(s, s_l, s_r)$, as well as the projections $x, x_l, x_r$ of those arcs onto the plane tangent to the polar axis, as shown in, for example, FIG. 20. To do this the equations derived in Case III are used as follows:

$$s = R\theta + R \sin^{-1}\left(\frac{h-R}{R} \sin \theta\right) \quad \text{Eqn. (31)}$$

$$s_l = R\left(\theta + \frac{1}{2}\Delta\theta\right) + R \sin^{-1}\left(\frac{h-R}{R} \sin\left(\theta + \frac{1}{2}\Delta\theta\right)\right) \quad \text{Eqn. (32)}$$

$$s_r = R\left(\theta - \frac{1}{2}\Delta\theta\right) + R \sin^{-1}\left(\frac{h-R}{R} \sin\left(\theta - \frac{1}{2}\Delta\theta\right)\right) \quad \text{Eqn. (33)}$$

$$x = \sin \theta \sqrt{R^2 - (h-R)^2 \sin^2 \theta} + \frac{1}{2}(h-R) \sin 2\theta \quad \text{Eqn. (34)}$$

$$x_l = \sin\left(\theta + \frac{1}{2}\Delta\theta\right)\sqrt{R^2 - (h-R)^2 \sin^2\left(\theta + \frac{1}{2}\Delta\theta\right)} + \frac{1}{2}(h-R) \sin(2\theta + \Delta\theta) \quad \text{Eqn. (35)}$$

$$x_r = \sin\left(\theta - \frac{1}{2}\Delta\theta\right)\sqrt{R^2 - (h-R)^2 \sin^2\left(\theta - \frac{1}{2}\Delta\theta\right)} + \frac{1}{2}(h-R) \sin(2\theta - \Delta\theta) \quad \text{Eqn. (36)}$$

Figure 26:
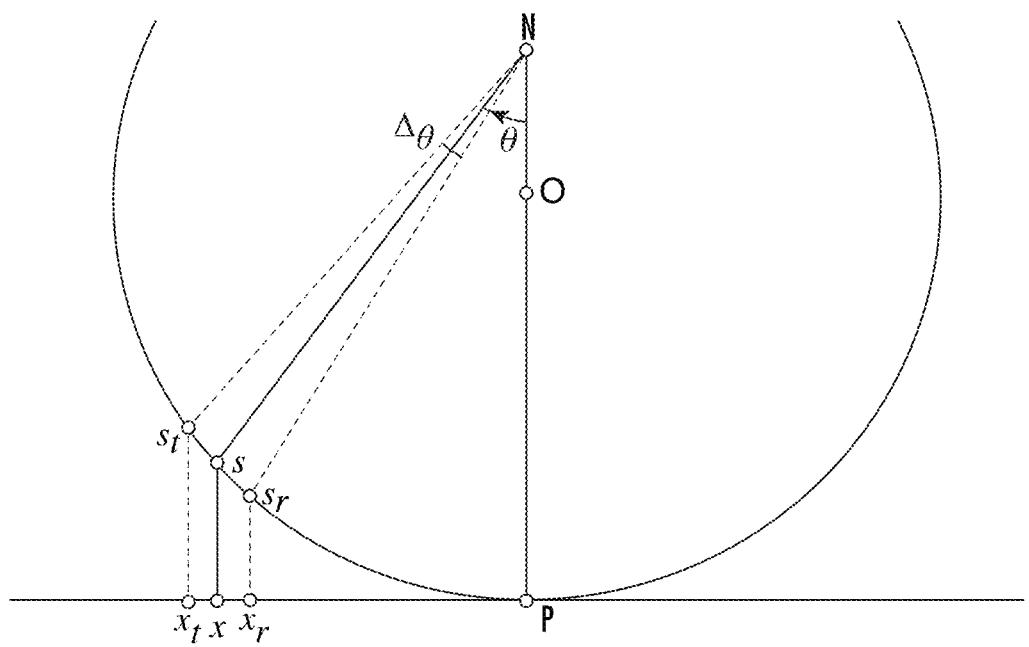
FIG. 26 illustrates projections x, $x_l$, $x_r$, of arcs onto the plane tangent to the polar axis according to some embodiments of the present inventive concept.

The positioning of the markings are diagrammed in FIG. 26.

Figure 27:
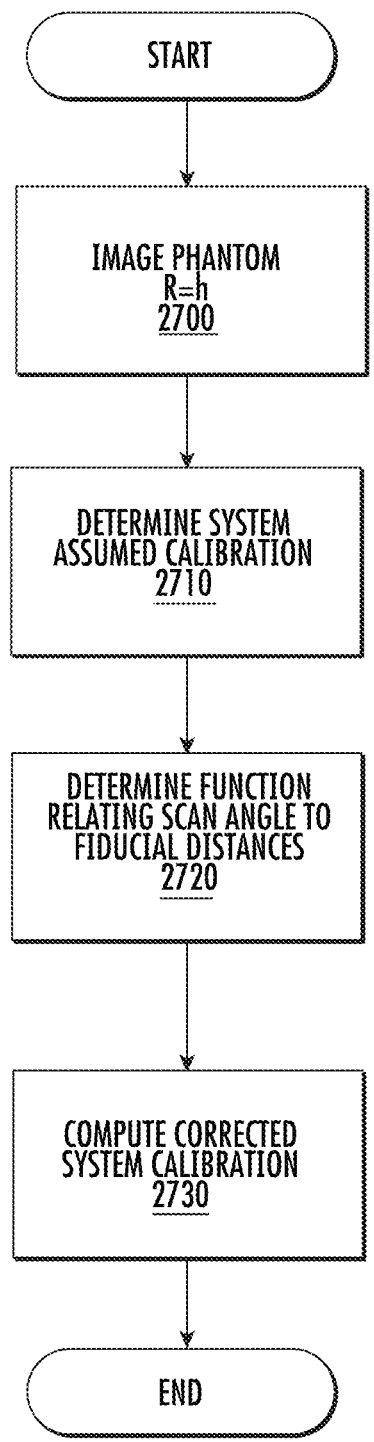
FIGS. 27 through 29 are flowcharts illustrating various operations in accordance with some embodiments of the present inventive concept.

From this, the following calibration steps are deduced, using the calibration phantom of the present inventive concept. The calibration steps in accordance with some embodiments of the present inventive concept will now be discussed with respect to the flowchart of FIG. 27. As illustrated in FIG. 27, operations begin at block 2700 by imaging a phantom when R=h. In particular, a B-scan of a calibration phantom including SME (R=h) is obtained (1). Once the scan is obtained, the original system calibration is deduced (block 2710). Based on the reflective patterns observed in the obtained OCT image, the lateral OCT image coordinates $y_i$ that correspond to the fiducial markings with known arc lengths $s_i$, as measured from the pole P along the curved posterior surface of the imaging phantom are identified (2). The function relating scan angle to fiducial distances is determined (block 2720). The scan angle $\theta_i$ that corresponds to each arc length $s_i$ is determined by exploiting the fact that the scan angle is equal to the central angle, so $$\theta_i = \frac{s_i}{R},$$

where R=h is the radius of curvature of the posterior surface of the phantom (3). A formula $\theta_i = f(y_i)$ that maps the lateral coordinate from the OCT image to the scan angle is obtained by fitting the data from previous step (3) to an appropriate model function (4). Extrapolate from this model in previous step (4) to determine $\theta_{max} = f(y_{max})$ (5). A corrected system calibration is then computed (block 2730). The presumed posterior chamber length $$h^* = \frac{y_{max}}{\tan \theta_{max}}$$

is computed (6).

Figure 28:
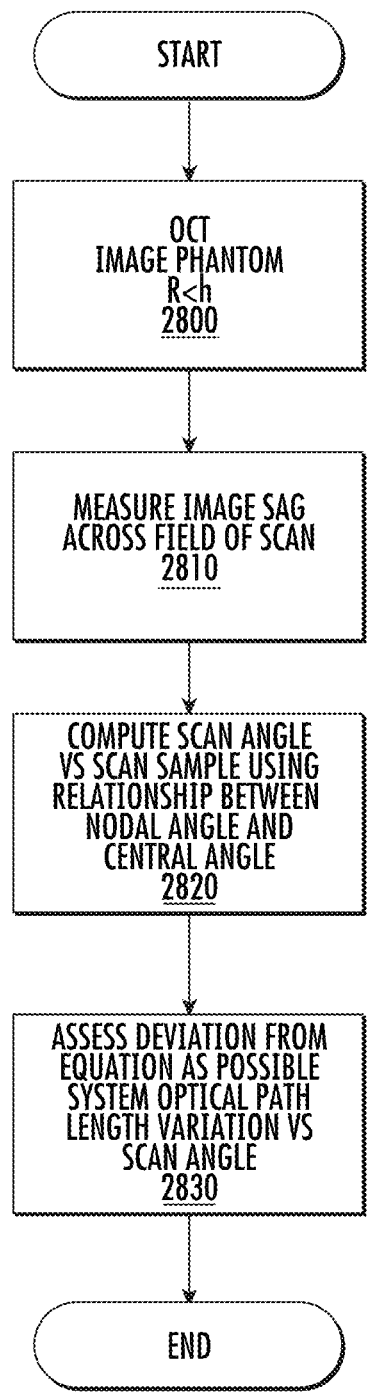

Operations for confirming that relationship between the lateral coordinate and the scan angle is linear, and to validate the scan angles computed above using an Anatomical Model Eye will be discussed with respect to the flowchart of FIG. 28. Operations begin at block 2800 by imaging a phantom when R<h or h>R. A B-scan of a calibration phantom is obtained including an Anatomical Model Eye (h>R) (1). The image sag is measured across the field of the scan (block 2810). The distance from the top of the B-scan frame to the retina surface, $z_i$, along each A-scan is measured (2). The scan angle versus scan sample is computed using the relationship between the nodal angle and the central angle (block 2820). The scan angle at each position using the relationship is calculated as follows:

$$\theta(y_i) = \cos^{-1}\left(\frac{\frac{1}{2}(z_0 - z_i)^2 - h(z_0 - z_i + R) + h^2}{(h - (z_0 - z_i))(h - R)}\right).$$

where $z_0$ is measured along the imaging axis (3). The deviation from the equation is assessed (block 2830). A regression analysis may be performed to test linearity (4).

Figure 29:
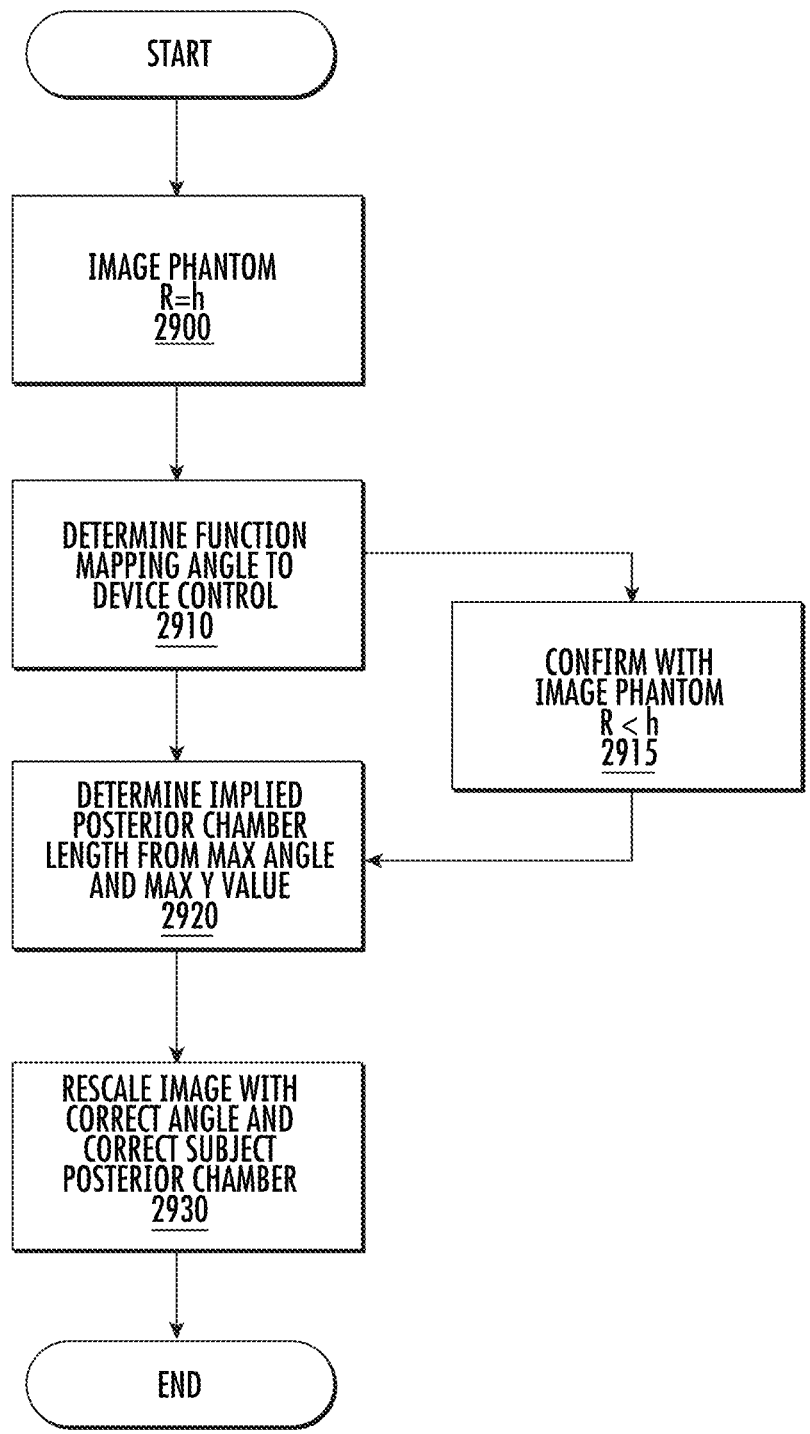

Another calibration methodology using one or both of the Spherical Model Eye (SME) and the Anatomical Model Eye (AME) is diagrammed in FIG. 29. A calibration image is acquired of the SME (block 2900). The function that maps the true angle to the system control function is deduced using the SME backplane (block 2910) as discussed above. The implied posterior chamber length h* of the original calibration is deduced from, e.g., $h^* = y^*_{max}/\tan(\theta_{max})$ (block 2920). Subsequent images may be rescaled using $y_{max} = h/\tan(\theta_{max})$ applying the function $y_i = f(\theta_i)$ to eliminate any distortion in the sampling function (block 2930). The calibration may be validated using the AME (block 2915).

Using these calibration methods, a Maxwellian-view imaging system that is calibrated to a cartesian scale in the lateral direction with a presumed ocular biometry can be transformed to a spherical polar coordinate scale that is more reflective of the actual topography of a retina, and can be rescaled according to the actual biometry of the eye under examination.

Figure 11C:
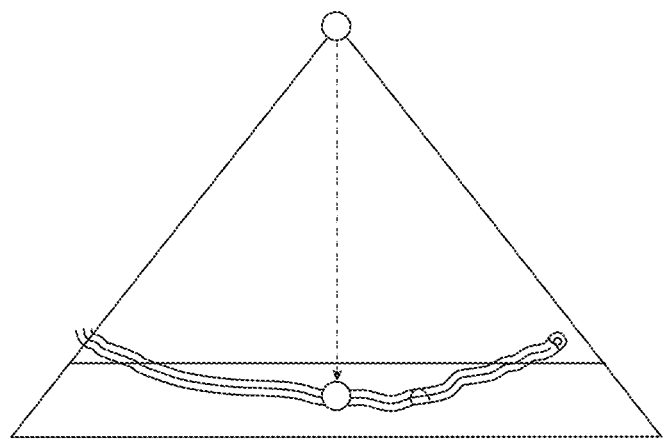

In some embodiments embodiment of the present inventive concept, a software utility combines a retinal image from a previously calibrated system with a new calibration set obtained by imaging a calibration phantom and a measure of the posterior chamber length of the eye under examination and rescales the first image into a second image that more accurately represents the dimensions of the retina under examination. In some embodiments, the software utility generates a new image in polar coordinates. In still a further embodiment, the new image accurately represents the image as a conical cross-section of the retina under test, as represented in FIG. 11C.

Further, as may be observed and understood from the equations and FIG. 11A, a system may be directly calibrated in polar coordinates, for example, A-scan position as a function of angle, using the calibration phantom of the present inventive concept. The polar representation is independent of ocular biometry and therefore images from correctly calibrated systems are immediately more interoperable as key assumptions that may differ between systems are removed from the polar representation of the retina. Adding biometry information, the polar coordinates are readily transformed to cartesian measures of the distance along the retina using s=h*θ where s is the arc length along the retina and h is the posterior chamber length of the eye under examination. This removes the ambiguity associated with the tan(θ), is more accurate and physiologically relevant, and has the distinct advantage of being simpler to implement and use.

Figure 30:
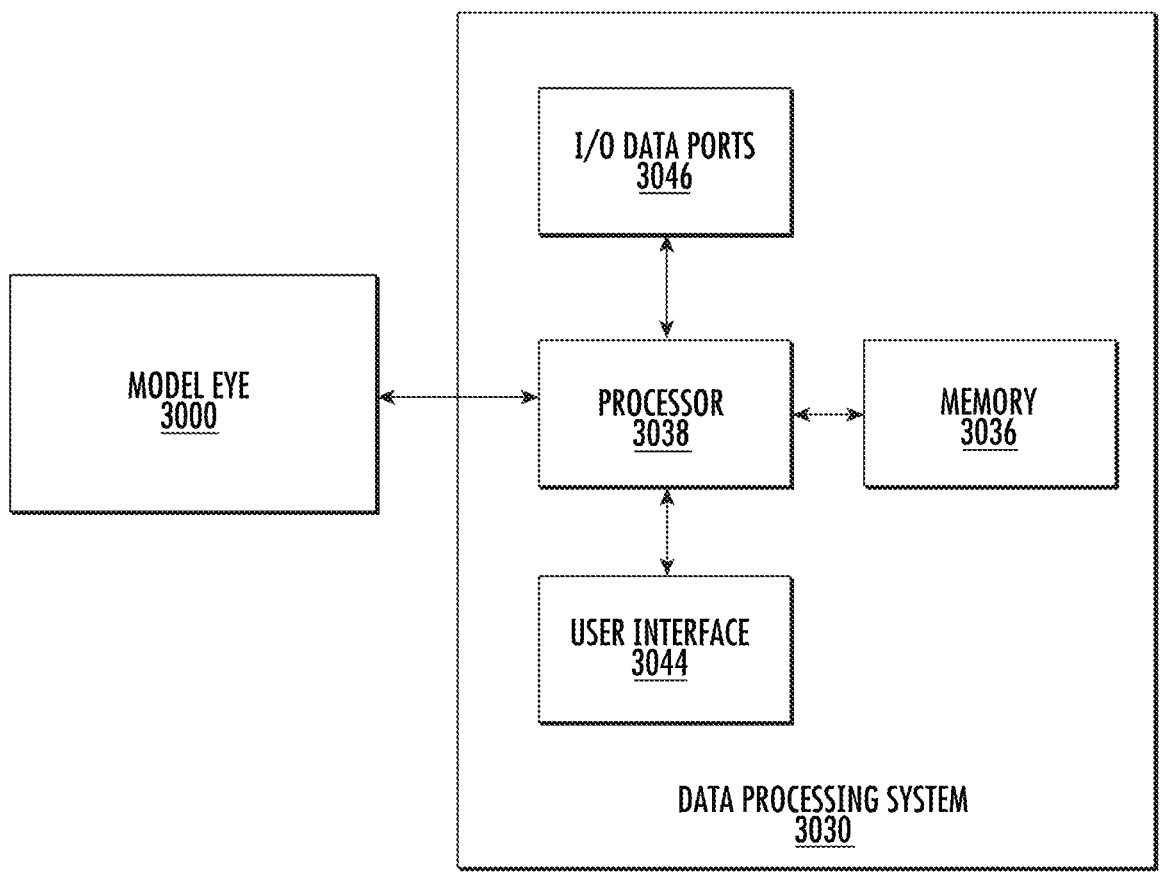
FIG. 30 is a block diagram of a data processing system for use in accordance with some embodiments of the present inventive concept.

As is clear from the details of the present inventive concept, embodiments of the present inventive concept require data processing. Referring now to FIG. 30, an example of a data processing system 3030 suitable for use with any of the examples described above will be discussed. Although the example data processing system 3030 is shown as in communication with a model eye 3000 in accordance with embodiments of the present inventive concept, the data processing system 3030 may be part of any component of the system without departing from the scope of the present inventive concept. In some examples, the data processing system 3030 can be any suitable computing device for performing operations according to the embodiments discussed herein described herein.

As illustrated, the data processing system 3030 includes a processor 3048 communicatively coupled to I/O components 3046, a user interface 3044 and a memory 3036. The processor 3048 can include one or more commercially available processors, embedded processors, secure processors, microprocessors, dual microprocessors, multi-core processors, other multi-processor architectures, another suitable processing device, or any combination of these. The memory 3036, which can be any suitable tangible (and non-transitory) computer-readable medium such as random access memory (RAM), read-only memory (ROM), erasable and electronically programmable read-only memory (EEPROMs), or the like, embodies program components that configure operation of the data processing system 630.

I/O components 3046 may be used to facilitate wired or wireless connections to devices such as one or more displays, game controllers, keyboards, mice, joysticks, cameras, buttons, speakers, microphones and/or other hardware used to input or output data. Memory 3036 represents nonvolatile storages such as magnetic, optical, or other storage media included in the data processing system and/or coupled to processor 3048.

The user interface 3044 may include, for example, a keyboard, keypad, touchpad, voice activation circuit, display or the like and the processor 3048 may execute program code or instructions stored in memory 3036.

It should be appreciated that data processing system 3030 may also include additional processors, additional storage, and a computer-readable medium (not shown). The processor(s) 3048 may execute additional computer-executable program instructions stored in memory 3036. Such processors may include a microprocessor, digital signal processor, application-specific integrated circuit, field programmable gate arrays, programmable interrupt controllers, programmable logic devices, programmable read-only memories, electronically programmable read-only memories, or other similar devices.

The aforementioned flow logic and/or methods show the functionality and operation of various services and applications described herein. If embodied in software, each block may represent a module, segment, or portion of code that includes program instructions to implement the specified logical function(s). The program instructions may be embodied in the form of source code that includes human-readable statements written in a programming language or machine code that includes numerical instructions recognizable by a suitable execution system such as a processor in a computer system or other system. The machine code may be converted from the source code, etc. Other suitable types of code include compiled code, interpreted code, executable code, static code, dynamic code, object-oriented code, visual code, and the like. The examples are not limited in this context.

If embodied in hardware, each block may represent a circuit or a number of interconnected circuits to implement the specified logical function(s). A circuit can include any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Qualcomm® Snapdragon®; Intel® Celeron®, Core (2) Duo®, Core i3, Core i5, Core i7, Itanium®, Pentium®, Xeon®, Atom® and XScale® processors; and similar processors. Other types of multi-core processors and other multi-processor architectures may also be employed as part of the circuitry. According to some examples, circuitry may also include an application specific integrated circuit (ASIC) or a field programmable gate array (FPGA), and modules may be implemented as hardware elements of the ASIC or the FPGA. Further, embodiments may be provided in the form of a chip, chipset or package.

Although the aforementioned flow logic and/or methods each show a specific order of execution, it is understood that the order of execution may differ from that which is depicted. Also, operations shown in succession in the flowcharts may be able to be executed concurrently or with partial concurrence. Further, in some embodiments, one or more of the operations may be skipped or omitted. In addition, any number of counters, state variables, warning semaphores, or messages might be added to the logical flows or methods described herein, for purposes of enhanced utility, accounting, performance measurement, or providing troubleshooting aids, etc. It is understood that all such variations are within the scope of the present disclosure. Moreover, not all operations illustrated in a flow logic or method may be required for a novel implementation.

Where any operation or component discussed herein is implemented in the form of software, any one of a number of programming languages may be employed such as, for example, C, C++, C#, Objective C, Java, Javascript, Perl, PUP, Visual Basic, Python, Ruby, Delphi, Flash, or other programming languages. Software components are stored in a memory and are executable by a processor. In this respect, the term "executable" means a program file that is in a form that can ultimately be run by a processor. Examples of executable programs may be, for example, a compiled program that can be translated into machine code in a format that can be loaded into a random access portion of a memory and run by a processor, source code that may be expressed in proper format such as object code that is capable of being loaded into a random access portion of a memory and executed by a processor, or source code that may be interpreted by another executable program to generate instructions in a random access portion of a memory to be executed by a processor, etc. An executable program may be stored in any portion or component of a memory. In the context of the present disclosure, a "computer-readable medium" can be any medium (e.g., memory) that can contain, store, or maintain the logic or application described herein for use by or in connection with the instruction execution system.

A memory is defined herein as an article of manufacture and including volatile and/or non-volatile memory, removable and/or non-removable memory, erasable and/or non-erasable memory, writeable and/or re-writeable memory, and so forth. Volatile components are those that do not retain data values upon loss of power. Nonvolatile components are those that retain data upon a loss of power. Thus, a memory may include, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may include, for example, static random access memory (SRAM), dynamic random access memory (DRAM), or magnetic random access memory (MRAM) and other such devices. The ROM may include, for example, a programmable read-only memory (PROM), an erasable programmable read-only memory (EPROM), an electrically erasable programmable read-only memory (EEPROM), or other like memory device.

The devices described herein may include multiple processors and multiple memories that operate in parallel processing circuits, respectively. In such a case, a local interface, such as a communication bus, may facilitate communication between any two of the multiple processors, between any processor and any of the memories, or between any two of the memories, etc. A local interface may include additional systems designed to coordinate this communication, including, for example, performing load balancing. A processor may be of electrical or of some other available construction.

It should be emphasized that the above-described embodiments of the present disclosure are merely possible examples of implementations set forth for a clear understanding of the principles of the disclosure. It is, of course, not possible to describe every conceivable combination of components and/or methodologies, but one of ordinary skill in the art may recognize that many further combinations and permutations are possible. That is, many variations and modifications may be made to the above-described embodiment(s) without departing substantially from the spirit and principles of the disclosure. All such modifications and variations are intended to be included herein within the scope of this disclosure and protected by the following claims.

That which is claimed is:

1. A model eye for calibrating a retinal imaging system, the retinal imaging system including a centered optical imaging system having first and second converging optical elements, an aperture stop of fixed or variable diameter D1 characterized by an optical axis, a nodal point, a focal plane, and a field of view ($2\theta$), the model eye comprising:
   a backplane having a negative radius of curvature R centered on the optical axis and a clear aperture diameter D2;
   a distance h along the optical axis from the nodal point to the backplane;
   an unobstructed field of view $2\theta$, where $\theta$ is an angle measured from the optical axis at the nodal point to an edge of the backplane at a radial limit of a clear aperture;
   a housing for enclosing elements of the model eye;
   a mechanical system for mounting, aligning, and preserving spacings of the elements of the model eye in the housings; and
   a pattern applied to the backplane, the pattern having a rotational symmetry and a radial repeating unit, extending substantially across the clear aperture, that spatially modulates intensity of light reflected from, or transmitted through, a surface of the backplane, wherein D2/D1 is greater than 2, an absolute value of R/h is greater than 0.5, and 2θ is greater than zero (0) degrees.

2. The eye model of claim 1, wherein a ratio of the radius of curvature R of the backplane to a posterior length L is such that 2.0 is greater than an absolute value of R/h which is greater than 0.50.

3. The eye model of claim 1, wherein a ratio of the radius of curvature R of the backplane to a posterior length L is such that 7/8 is greater than an absolute value of R/h which is greater than 2/3.

4. The eye model of claim 1, wherein a ratio of the radius of curvature R of the backplane to a posterior length L is such that 1.10 is greater than an absolute value of R/h which is greater than 0.90.

5. The eye model of claim 1, wherein a ratio of the radius of curvature R of the backplane to a posterior length L is such that 1.05 is greater than an absolute value of R/L which is greater than 0.95.

6. The eye model of claim 1, wherein the field of view 2θ is greater than 60 degrees.

7. The eye model of claim 1, wherein the field of view 2θ is greater than 80 degrees.

8. The eye model of claim 1, wherein the field of view 2θ is greater than 100 degrees.

9. The eye model of claim 1, wherein the applied pattern comprises a series of concentric annular rings, the series of concentric annular rings including:
   a first annulus having a first diameter D3 and a width W, where 10 is greater than D/W which is greater than 2.5;
   a second annulus having a second diameter D4 that is at least 2 times the diameter D3 of the first annulus and no greater than 4 times the diameter D3 of the first annulus; and
   a series of successive non-intersecting annular rings that extend across at least 80 percent of the field of view.

10. The eye model of claim 9, wherein the applied pattern comprises a symmetry breaking feature set, the symmetry breaking feature set being sufficient to indicate a degree of rotation of the eye model about the optical axis when imaged from a perspective of a Maxwellian-view imaging device.

11. The eye model of claim 10, wherein the symmetry breaking feature set further comprises first and second orientations rotated about the optical axis by 90 degrees sufficient to mimic a horizontal inversion when imaged from a perspective of a Maxwellian-view imaging device.

12. The eye model of claim 1:
   wherein the applied pattern comprises a series of repeated shapes for testing lateral resolution at multiple positions within the field of view;
   wherein the fiducials consist of one of a series of similar shapes reproduced over a range of scales and a series of shapes at a common scale bundled into successive larger units;
   where the bundles successive larger units approximate an original shape at successively larger scale.

13. The eye model of claim 12, wherein the repeated shapes comprise circles organized into one of hexlets, Steiner Chains and Apollonian Circle Packings.

* * * * *